United States Patent [19]

Cederhom-Williams

[11] Patent Number: 6,083,902
[45] Date of Patent: *Jul. 4, 2000

[54] RECOMBINANT FIBRIN CHAINS, FIBRIN AND FIBRIN-HOMOLOGS

[75] Inventor: Stewart Anthony Cederhom-Williams, Littlemore, United Kingdom

[73] Assignee: Bristol-Myers Squibb Company, New York, N.Y.

[*] Notice: This patent issued on a continued prosecution application filed under 37 CFR 1.53(d), and is subject to the twenty year patent term provisions of 35 U.S.C. 154(a)(2).

[21] Appl. No.: 08/434,099

[22] Filed: May 3, 1995

Related U.S. Application Data

[63] Continuation-in-part of application No. 08/236,979, May 2, 1994, abandoned.

[51] Int. Cl.[7] .................. A61K 38/16; C07K 14/435; C12N 5/10; C12N 1/21
[52] U.S. Cl. .................. 514/2; 514/12; 435/69.1; 435/252.3; 435/325; 530/382; 536/23.5; 536/23.1
[58] Field of Search .................. 435/69.1, 240.1, 435/243, 252.3, 254.11, 325; 514/2, 12; 530/382, 350; 536/23.5, 23.1

[56] References Cited

U.S. PATENT DOCUMENTS

| | | | |
|---|---|---|---|
| 4,902,281 | 2/1990 | Avoy | 604/191 |
| 5,120,834 | 6/1992 | Gargan et al. | 530/388 |
| 5,124,439 | 6/1992 | Nieuwenhuizen | 530/387.9 |
| 5,292,362 | 3/1994 | Bass et al. | 106/124 |
| 5,330,974 | 7/1994 | Pines et al. | 514/21 |
| 5,453,359 | 9/1995 | Gargan et al. | 435/13 |
| 5,510,102 | 4/1996 | Cochrum | 424/78.08 |
| 5,631,011 | 5/1997 | Wadström | 424/400 |
| 5,639,940 | 6/1997 | Garner et al. | 800/2 |

FOREIGN PATENT DOCUMENTS

| | | |
|---|---|---|
| 0 068 149 A2 | 1/1983 | European Pat. Off. |
| 0472205 | 5/1991 | European Pat. Off. |
| 0592242A1 | 4/1994 | European Pat. Off. |

OTHER PUBLICATIONS

Bolyard and Lord, "Expression in *Escherichia coli* of the Human Fibrinogen Bβ Chain and Its Cleavage by Thrombin," Blood, Apr. 1989, vol. 73, No. 5, pp 1202–1206.

Bolyard and Lord, "High–level expression of a functional human fibrinogen gamma chain in *Escherichia coli*," Gene, (1988), 66:183–192.

Brennan, "Fibrin Glue," Blood Reviews, (1991), 5:240–244.

Chevalet et al., "Genetic Improvements of an Industrial Strain of *Aspergillus flavus* for Urate Oxidase Production," Journal of Biotechnology, (1993) 27:239–247.

Chung et al., "Characterization of Complementary Deoxyribonucleic Acid and Genomic Deoxyribonucleic Acid for the β Chain of Human Fibrinogen," Biochemistry, (1983), 22:3244–3250.

Chung et al., "Characterization of a cDNA Clone Coding for the βChain of Bovine Fibrinogen," Proc. Natl. Acad. Sci. U.S.A., Mar. 1981, vol. 78, No. 3, pp 1466–1470.

Chung et al., "Cloning of Fibrinogen Genes and Their cDNA," Ann. N.Y. Acad. Sci., (1983), 408:449–456.

Chung et al., "Characterization of a Complementary Deoxyribonucleic Acid Coding for the γ Chain of Human Fibrinogen," Biochemistry, (1983), 22:3250–3256.

Danishefsky et al., "Intracellular Fate of Fibrinogen Bβ Chain Expressed in COS Cells," Biochemica et Biophysica Acta, (1990), 1048:202–208.

Emr, "Heterologous Gene Expression in Yeast," Methods in Enzymology, (1990), 185:231–233.

Farrell et al., "Processing of the Carboxyl 15–Amino Acid Extension in the α–Chain of Fibrinogen," The Journal of Biological Chemistry, May 15, 1993, vol. 268, No. 14, pp 10351–10355.

Farrell et al., "Recombinant human fibrinogen and sulfation of the γ' chain," Biochemistry, (1991), 30:9414–9420.

Fischer et al., "Renaturation of Lysozyme—Temperature Dependency of Renaturation Rate, Renaturation Yield, and Aggregation: Identification of Hydrophobic Folding Intermediates," Archives of Biochemistry and Biophysics, Oct. 1993, vol. 306, No. 1, pp 183–187.

(List continued on next page.)

*Primary Examiner*—Elizabeth Kemmerer
*Attorney, Agent, or Firm*—Theodore R. Furman, Jr.; John M. Kilcoyne

[57] ABSTRACT

The invention is directed to fibrin materials for use in fibrin compositions and methods that avoid the need to use thrombin as an activating agent for fibrin monomer-based sealants. The invention provides for substantially pure fibrin chains, fibrin chain precursors, fibrin chains with other N-terminal extensions, fibrin monomer, fibrin-homolog and fibrin-analog. The invention further provides for variant fibrin γ-chains. The variant gamma-chain contains one or more mutations and/or deletions in the C-terminal region following the coiled-coil forming region such that, when incorporated into fibrin-homolog, the homolog lacks the ability to self-polymerize but has the ability to form non-covalent bonds, and thereby form mixed polymers useful as sealants, with fibrinogen. The invention also provides nucleotide sequences encoding fibrin chains or fibrin chain variants and cells expressing fibrin chains, fibrin chain variants, fibrin monomer, fibrin precursor or fibrinogen-analog. The invention further provides a method of forming fibrin-related proteins in vitro from their component fibrin chains. The invention additionally provides a method for forming a fibrin sealant by a reacting a first fibrin-related protein that is incapable of self-polymerizing with a second fibrin-related protein that is incapable of self-polymerizing. Fibrin chains produced by methods of the present invention may be used as sources of substantially pure starting material for the production of important fibrin-derived factors that regulate angiogenesis, platelet aggregation, and other physiological processes.

29 Claims, 6 Drawing Sheets

OTHER PUBLICATIONS

Gan et al., "Reconstitution of Catalytically Compotent Human ζ–Thrombin by Combination of ζ–Thrombin Residues A1–36 and B1–148 and an *Escherichia coli* Expressed Polypeptide Corresponding to ζ–Thrombin Residues B149–259," Biochemistry, (1991), 30:11694–11699.

Grunfeld et al., "Effector–Assisted Refolding of Recombinant Tissue–Plasminogen Activator Produced in *Escherichia coli*," Applied Biochemistry and Biotechnology, (1992), 33:117–138.

Hartwig and Danishefsky, "Studies on the Assembly and Secretion of Fibrinogen," The Journal of Biological Chemistry, Apr. 5, 1991, vol. 266, No. 10, pp 6578–6585.

Hirose et al., "Renaturation of Ovotransferrin Under Two–step Conditions Allowing Primary Folding of the Fully Reduced Form and the Subsequent Regeneration of the Intramolecular Disulfides," The Journal of Biological Chemistry, Oct. 5, 1989, vol. 264, No. 28, pp 16867–16872.

Huang et al., "Biosynthesis of Human Fibrinogen, Subunit Interactions and Potential Intermediates in the Assembly," The Journal of Biological Chemistry, Apr. 25, 1993, vol. 268, No. 12, pp 8919–8926.

Kingsman et al., "Heterologous Gene Expression in *Saccharomyces cerevisiae*," Biotechnology and Genetic Engineering Reviews, Sep. 1985, 3:377–416.

Lord and Fowlkes, "Expression of a Fibrinogen Fusion Peptide in *Escherichia coli*: A Model Thrombin Substrate for Structure/Function Analysis," Blood, Jan. 1989, vol. 73, No. 1, pp 166–171.

Matras, "Fibrin Seal: The State of the Art," The Journal of Oral Maxillofacial Surgery, (1985), 13:605–611.

Mosesson, "The Assembly and Structure of the Fibrin Clot," Nouv. Rev. Fr. Hematol., (1992), 34:11–16.

Orsini et al., "Efficient renaturation and Fibrinolytic Properties of Prourokinase and a Deletion Mutant Expressed in *Escherichia coli* as Inclusion Bodies," Eur. J. Biochem., (1991) 195:691–697.

Rinas et al., "Denaturation–Renaturation of the Fibrin–Stabilizing Factor XIII a–Chain Isolated from Human Placenta, Properties of the Native and Reconstituted Protein," Biol. Chem. Hoppe–Seyler, Jan. 1990, 371:49–56.

Rixon et al., "Nucleotide Sequence of the Gene for the γ Chain of Human Fibrinogen," Biochemistry, (1985), 24:2077–2086.

Rixon et al., "Characterization of a Complementary Deoxyribonucleic Acid Coding for the α Chain of Human Fibrinogen," Biochemistry, (1983), 22:3237–3244.

Roberts et al., "Heterologous Gene Expression in *Aspergillus niger*: a Glucoamylase–porcine Pancreatic Prophospholipase $A_2$ Fusion Protein is Secreted and Processed to Yield Mature Enzyme," Gene, (1992), 122:155–161.

Roy et al., "Regulation of Fibrinogen Assembly: Transfection of Hep G2 Cells with Bβ cDNA Specifically Enhances Synthesis of the Three Component Chains of Fibrinogen," The Journal of Biological Chemistry, Apr. 15, 1990, vol. 265, No. 11, pp 6389–6393.

Roy et al., "Assembly and Secretion of Recombinant Human Fibrinogen," The Journal of Biological Chemistry, Mar. 15, 1991, vol. 266, No. 8, pp 4758–4763.

Roy et al., "Assembly and Secretion of Fibrinogen: Degradation of Individual Chains," The Journal of Biological Chemistry, Nov. 15, 1992, vol. 267, No. 32, pp 23151–23158.

Rudolph, "Folding for Profit: Renaturation of Recombinant Proteins from Inclusion Bodies as a New Downstream Process," Boehringer Manneheim GmbH, pp 295–297.

Rudolph, "Renaturation of Recombinant, Disulfide–bonded Proteins from "Inclusion Bodies"," Boehringer Manneheim GmbH, pp 149–171.

Tsuchiya et al., "High Level Expression of the Synthetic Human Lysozyme Gene in *Aspergillus oryzae*," Appl. Microbiol. Biotechnol., (1992), 38:109–114.

Van den Berg et al., "Kluyveromyces as a Host for Heterologous Gene Expression: Expression and Secretion of Prochymosin," Bio/Technology, Feb. 1990, 8:135–139.

Wingfield and Dickinson, "Increased Activity of a Model Heterologous Protein in *Saccharomyces cerevisiae* Strains with Reduced Vacuolar Proteinases," Microbiology and Biotechnology, (1993) pp 211–215.

Zhang et al., "Symmetrical Disulfide Bonds are not Necessary for Assembly and Secretion of Human Fibrinogen," The Journal of Biological Chemistry, May 25, 1993, vol. 268, No. 15, pp 11278–11282.

Zhang and Redman, "Identification of Bβ Chain Domains Involved in Human Fibrinogen Assembly," The Journal of Biological Chemistry, Oct. 25, 1992, vol. 267, No. 30, pp 21727–21732.

Hettasch et al., "The Residues AGDV of Recombinant γ Chains of Human Fibrinogen Must Be Carboxy–Terminal to Support Human Platelet Aggregation," Thrombosis and Haemostatis, F.K. Schnattauer Verlagsgesellschaft mbH (Stuttgart), Jul. 17, 1992.

Procyk et al., Nonclottable Fibrin Obtained from Partially Reduced Fibrinogen: Characterization and Tissue Plasminogen Activator Stimulation, Biochemistry, vol. 31, No. 8, 1992.

Bolyard et al. High–level expression of a functional human fibrinogen gamma chain in *Escherichia coli*. Gene. vol. 66, pp. 183–192, 1988.

Bolyard et al. Mutagenesis of human fibrinogen γchain 259–411 synthesized in *E. coli*: further characterization of the role of the disulfide bond Cys326–Cys339 in calcium binding. Biochemical and Biophysical Research Communications. vol. 174, No. 2, pag, Jan. 31, 1991.

Henschen. Human fibrinogen—structural variants and functional sites. Thrombosis and Haemostasis. vol. 70, No. 1, pp. 42–47, Jul. 1, 1993.

Horwitz et al. Localization of a fibrinδ–chain polymerization site within segment Thr–374 to Glu–396 of human fibrinogen. Proceedings of the National Academy of Sciences, USA. vol. 81, pp. 5980–5984, Oct. 1984.

Mimuro et al. Gene analysis of abnormal fibrinogens with a mutation in the δchain. International Journal of Hematology. vol. 56, pp. 129–134, 1992.

Rosenberg et al. Paris I dysfibrinogenemia: a point mutation in intron 8 results in insertion of a 15 amino acid sequence in the fibrinogen δ–chain. Thrombosis and Haemostasis. vol. 69, No. 3, pp. 217–220, 1993.

Steinmann et al. A new substitution, δ 358 Ser → Cys, in fibrinogen Milano VII causes defective fibrin polymerization. Blood. vol. 84, No. 6, pp. 1874–1880, Sep. 15, 1994.

Terukina et al. Substitution of δArg–275 by Cys in an abnormal fibrinogen, "Fibrinogen Osaka II." The Journal of Biological Chemistry. vol. 263, No. 27, pp. 13579–13587, Sep. 25, 1988.

Varadi et al. Localization of segments essential for polymerization and for calcium binding in the δ–chain of human fibrinogen. Biochemistry. vol. 25, No. 25, pp. 519–528, Feb. 11, 1986.

Carter, "Site–Specific Proteolysis of Fusion Proteins," Chapter 13, 181–192, in Protein Purification: From Molecular Mechanism to Large–Scale Processes, eds. Ladisch et al., 1990, *American Chemical Society*, Washington, D.C., 280 pp.

Lord, "Expression of a Cloned Human Fibrinogen cDNA in *Escherichia coli*: Synthesis of an A Alpha Polypeptide," *DNA*, 4:33–38, 1985.

Lord, "Analysis of Fibrinogen Aα–fusion Proteins," *The Journal of Biological Chemistry*, 265:838–843, 1990.

Reber et al., "Fibrinogen Bergamo I (Aα 16Arg → Cys): Susceptibility Towards Thrombin Following Aminoethylation, Methylation or Carboxamidornethylation of Cysteine Residues," *Thrombosis and Hemostasis*, 54:390–393, 1985.

Procyk et al., Disulfide Bond Reduction in Fibrinogen: Calcium Protection and Effect on Clottability, Biochemistry 1990, 29, pp. 1501–1507.

M. Hiroaki. Production of Antimutagen. Patent Abstracts of Japan (European Patent Office). Pub. No. 03180191, Date: Jun. 8, 1991.

Koopman et al. Molecular Basis of Fibrinogen Naples Associated with Defective Thrombin Binding and Thrombophilia. J. Clin. Invest., vol. 90, Jul. 1992, pp. 238–244.

Redman et al. Fibrinogen (specification). U.S. Dept of Commerce, Mar. 4, 1991.

Roy et al. Overexpression of Any Fibrinogen Chain by Hep G2 Cells Specifically Elevates the Expression of the Other Two Chains. J. Biological Chemistry, vol. 269, No. 1, Jan. 7, 1994, pp. 691–695.

N. Yoshida et al. A New Congenital Abnormal Fibrinogen Ise Characterized by the Replacement of BB Glycine–15 by Cystein. Blood, vol. 77, No. 9, May 1, 1991, pp. 1958–1963.

KpnI
```
                             A1
     CGTCGACTAGGAGCCAGCCCCACCCTTAGAAAAGATGTTTTCCATGAGGATCGTC
 1   ----------+----------+----------+----------+----------+---------+   60
     CATGGCAGCTGATCCTCGGTCGGGGTGGGAATCTTTTCTACAAAAGGTACTCCTAGCAG
                             A2
             A3
     TGCCTGGTCCTAAGTGTGGTGGGCACAGCATGGACTGGCCCA
61   ----------+----------+----------+----------+---------+   107
     ACGGACCAGGATTCACACCACCCGTGTCGTACCTGACCGGGTGCGC
             A4
                                              MluI
```

FIG. 1

KpnI
```
                       B1
     CGTCGACATGAAAAGGATGGTTTCTTGGAGCTTCCACAAACTTAAAACCATGAAA
 1   ----------+----------+----------+----------+----------+----------+   60
     CATGGCAGCTGTACTTTTCCTACCAAAGAACCTCGAAGGTGTTTGAATTTTGGTACTTT
                                               B2
           B3
     CATCTATTATTGCTACTATTGTGTGTTTTTCTAGTTAAGTCCGGTCATCGACCCCTTGAC
61   ----------+----------+----------+----------+----------+----------+   120
     GTAGATAATAACGATGATAACACACAAAAAGATCAATTCAGGCCAGTAGCTGGGGAACTG
              B4
     B5
     AAGAAGAGAGAAGAGGCTCCA
121  ----------+----------+------   146
     TTCTTCTCTTCTCCGAGGTTCGA
     B6
            HindIII
```

FIG. 2

```
                                 NotI     HindIII
     AvrII                         |         |
                         G1
     CTAGGGGGAGCCAAACAGGCTGGAGACGTTTAAGCGGCCGCAAGCTTG
 1   ----------+----------+----------+----------+----------+----   54
     CCCCTCGGTTTGTCCGACCTCTGCAAATTCGCCGGCGTTCGAACTTAA
                         G2
                                                  EcoRI
```

FIG. 3

```
          KpnI  SalI
                 |
          5'-CATGGCAGCT-3"
```

5' END OF ADAPTOR MUST BE PHOSPHORYLATED

FIG. 4

ALPHA FIBRINOGEN:

PCR PRIMERS:

PCR1A: 5'-GGGAAGCTTACGCGTTGTGGAAAGACATCAATCT-3'

PCR2A: 5'-TAAGTGTTGCCTATCTCTAGA-3'

SYNTHETIC LEADER OLIGO.S:

A1: 5'-CGTCGACTAGGAGCCAGCCCCAGCCCCACCCTTAGAAAAGATGTTTTCCATGAG-3'

A2: 5'-CAGACGATCCTCATGGAAAACATCTTTTCTAAGGGTGGGGCTGGCTCCTAGTCGACGGTAC-3'

A3: 5'-GATCGTCTGCCTGGTCCTAAGTGTGGTGGGCACAGCATGGACTGGCCCA-3'

A4: 5'-CGCGTGGGCCAGTCCATGCTGTGCCCACCACACTTAGGACCAGG-3'

BETA FIBRINOGEN:

PCR PRIMERS:

PCR1B: 5'-TTTAAGCTTGAGGCCTGCCCCACCGC-3'

PCR2B: 5'-GCAACATTTCCAAATCCCTG-3'

SYNTHETIC LEADER OLIGO. S:

B1: 5'-CGTCGACATGAAAAGGATGGTTTCTTGGAGCTTCCACAAACT-3'

B2: 5'-ATGGTTTTAAGTTTGTGGAAGCTCCAAGAAACCATCCTTTTCATGTCGACGGTAC-3'

B3: 5'-TAAAACCATGAAACATCTATTATTGCTACTATTGTGTGTTTTTCTAGTT-3'

B4: 5'-ACCGGACTTAACTAGAAAAACACACAATAGTAGCAATAATAGATGTTTC-3'

B5: 5'-AAGTCCGGTCATCGACCCCTTGACAAGAAGAGAGAAGAGGCTCCA-3'

B6: 5'-AGCTTGGAGCCTCTTCTCTCTTCTTGTCAAGGGGTCGATG-3'

GAMMA FIBRINOGEN:

PCR PRIMERS:

PCR1G: 5'-CACTCCCATAATGGCATGC-3'

PCR2G: 5'-CACGAATTCCCTAGGTGGTGTTGCTGTCC-3'

SYNTHETIC 3' END FRAGMENT OLIGO. S:

G1: 5'-CTAGGGGGAGCCAAACAGGCTGGAGACGTTTAAGCGGCCGCAAGCTTG-3'

G2: 5'-AATTCAAGCTTGCGGCCGCTTAAACGTCTCCAGCCTGTTTGGCTCCCC-3'

KpnI/SalI ADAPTOR:

5'-CATGGCAGCT-3'

FIG. 5

```
      GGTACCGGGCCCCCCCTCGAGGTCGACCGCGGCCCCCCGGGCACTCAGACATCATGAGTT
  1   ------------+----------+----------+----------+----------+----------+   60
      CCATGGCCCGGGGGGGAGCTCCAGCTGGCGCCGGGGGGCCCGTGAGTCTGTAGTACTCAA

TyrArgAlaProProArgGlyArgProArgProProGlyHisSerAspIleMetSerTrp -

GGTCCTTGCACCCCCGGAATTTAATTCTCTACTTCTATGCTCTTTTATTTCTCTCTTCAA
  61  ------------+----------+----------+----------+----------+----------+   120
      CCAGGAACGTGGGGGCCTTAAATTAAGAGATGAAGATACGAGAAAATAAAGAGAGAAGTT

SerLeuHisProArgAsnLeuIleLeuTyrPheTyrAlaLeuLeuPheLeuSerSerThr -

CATGTGTAGCATATGTTGCTACCAGAGACAACTGCTGCATCTTAGATGAAAGATTCGGTA
 121  ------------+----------+----------+----------+----------+----------+   180
      GTACACATCGTATACAACGATGGTCTCTGTTGACGACGTAGAATCTACTTTCTAAGCCAT

CysValAlaTyrValAlaThrArgAspAsnCysCysIleLeuAspGluArgPheGlySer -

GTTATTGTCCAACTACCTGTGGCATTGCAGATTTCCTGTCTACTTATCAAACCAAAGTAG
 181  ------------+----------+----------+----------+----------+----------+   240
      CAATAACAGGTTGATGGACACCGTAACGTCTAAAGGACAGATGAATAGTTTGGTTTCATC

TyrCysProThrThrCysGlyIleAlaAspPheLeuSerThrTyrGlnThrLysValAsp -

ACAAGGATCTACAGTCTTTGGAAGACATCTTACATCAAGTTGAAAACAAAACATCAGAAG
 241  ------------+----------+----------+----------+----------+----------+   300
      TGTTCCTAGATGTCAGAAACCTTCTGTAGAATGTAGTTCAACTTTTGTTTTGTAGTCTTC

LysAspLeuGlnSerLeuGluAspIleLeuHisGlnValGluAsnLysThrSerGluVal -

TCAAACAGCTGATAAAAGCAATCCAACTCACTTATAATCCTGATGAATCATCAAAACCAG
 301  ------------+----------+----------+----------+----------+----------+   360
      AGTTTGTCGACTATTTTCGTTAGGTTGAGTGAATATTAGGACTACTTAGTAGTTTTGGTC

LysGlnLeuIleLysAlaIleGlnLeuThrTyrAsnProAspGluSerSerLysProAsp -

ATATGATAGACGCTGCTACTTTGAAGTCCAGGATAATGTTAGAAGAAATTATGAAATATG
 361  ------------+----------+----------+----------+----------+----------+   420
      TATACTATCTGCGACGATGAAACTTCAGGTCCTATTACAATCTTCTTTAATACTTTATAC

MetIleAspAlaAlaThrLeuLysSerArgIleMetLeuGluGluIleMetLysTyrGlu -

AAGCATCGATTTTAACACATGACTCAAGTATTCGGTATTTGCAGGAAATATATAATTCAA
 421  ------------+----------+----------+----------+----------+----------+   480
      TTCGTAGCTAAAATTGTGTACTGAGTTCATAAGCCATAAACGTCCTTTATATATTAAGTT

AlaSerIleLeuThrHisAspSerSerIleArgTyrLeuGlnGluIleTyrAsnSerAsn -

ATAATCAAAAGATTGTTAACCTGAAAGAGAAGGTAGCCCAGCTTGAAGCACAGTGCCAGG
 481  ------------+----------+----------+----------+----------+----------+   540
      TATTAGTTTTCTAACAATTGGACTTTCTCTTCCATCGGGTCGAACTTCGTGTCACGGTCC

AsnGlnLysIleValAsnLeuLysGluLysValAlaGlnLeuGluAlaGlnCysGlnGlu -

AACCTTGCAAAGACACGGTGCAAATCCATGATATCACTGGGAAAGATTGTCAAGACATTG
 541  ------------+----------+----------+----------+----------+----------+   600
      TTGGAACGTTTCTGTGCCACGTTTAGGTACTATAGTGACCCTTTCTAACAGTTCTGTAAC

ProCysLysAspThrValGlnIleHisAspIleThrGlyLysAspCysGlnAspIleAla -

CCAATAAGGGAGCTAAACAGAGCGGGCTTTACTTTATTAAACCTCTGAAAGCTAACCAGC
 601  ------------+----------+----------+----------+----------+----------+   660
      GGTTATTCCCTCGATTTGTCTCGCCCGAAATGAAATAATTTGGAGACTTTCGATTGGTCG
```

FIG. 7A

```
                  AsnLysGlyAlaLysGlnSerGlyLeuTyrPheIleLysProLeuLysAlaAsnGlnGln -
      AATTCTTAGTCTACTGTGAAATCGATGGGTCTGGAAATGGATGGACTGTGTTTCAGAAGA
661   ---------+---------+---------+---------+---------+---------+  720
      TTAAGAATCAGATGACACTTTAGCTACCCAGACCTTTACCTACCTGACACAAAGTCTTCT

PheLeuValTyrCysGluIleAspGlySerGlyAsnGlyTrpThrValPheGlnLysArg -
      GACTTGATGGCAGTGTAGATTTCAAGAAAAACTGGATTCAATATAAAGAAGGATTTGGAC
721   ---------+---------+---------+---------+---------+---------+  780
      CTGAACTACCGTCACATCTAAAGTTCTTTTTGACCTAAGTTATATTTCTTCCTAAACCTG

LeuAspGlySerValAspPheLysLysAsnTrpIleGlnTyrLysGluGlyPheGlyHis -
      ATCTGTCTCCTACTGGCACAACAGAATTTTGGCTGGGAAATGAGAAGATTCATTTGATAA
781   ---------+---------+---------+---------+---------+---------+  840
      TAGACAGAGGATGACCGTGTTGTCTTAAAACCGACCCTTTACTCTTCTAAGTAAACTATT

LeuSerProThrGlyThrThrGluPheTrpLeuGlyAsnGluLysIleHisLeuIleSer -
      GCACACAGTCTGCCATCCCATATGCATTAAGAGTGGAACTGGAAGACTGGAATGGCAGAA
841   ---------+---------+---------+---------+---------+---------+  900
      CGTGTGTCAGACGGTAGGGTATACGTAATTCTCACCTTGACCTTCTGACCTTACCGTCTT

ThrGlnSerAlaIleProTyrAlaLeuArgValGluLeuGluAspTrpAsnGlyArgThr -
      CCAGGACTGCAGACTATGCCATGTTCAAGGTGGGACCTGAAGCTGACAAGTACCGCCTAA
901   ---------+---------+---------+---------+---------+---------+  960
      GGTCCTGACGTCTGATACGGTACAAGTTCCACCCTGGACTTCGACTGTTCATGGCGGATT

ArgThrAlaAspTyrAlaMetPheLysValGlyProGluAlaAspLysTyrArgLeuThr -
      CATATGCCTACTTCGCTGGTGGGGATGCTGGAGATGCCTTTGATGGCTTTGATTTTGCG
961   ---------+---------+---------+---------+---------+---------+  1020
      GTATACGGATGAAGCGACCACCCCTACGACCTCTACGGAAACTACCGAAACTAAAACCGC

TyrAlaTyrPheAlaGlyGlyAspAlaGlyAspAlaPheAspGlyPheAspPheGlyAsp -
                  [SEQ4]                     SphI
      ATGATCCTAGTGACAAGTTTTTCACATCCCATAATGGCATGCAGTTCAGTACCTGGGACA
1021  ---------+---------+---------+---------+---------+---------+  1080
      TACTAGGATCACTGTTCAAAAAGTGTAGGGTATTACCGTACGTCAAGTCATGGACCCTGT

AspProSerAspLysPhePheThrSerHisAsnGlyMetGlnPheSerThrTrpAspAsn -
                                [MUT1G]                  [PCRX]
      ATGACAATGATAAGTTTGAAGGCAACGCTGCTGAACAGGATGGATCTGGTTGGTGGATGA
1081  ---------+---------+---------+---------+---------+---------+  1140
      TACTGTTACTATTCAAACTTCCGTTGCGACGACTTGTCCTACCTAGACCAACCACCTACT
                                                  [PCRY]

AspAsnAspLysPheGluGlyAsnAlaAlaGluGlnAspGlySerGlyTrpTrpMetAsn -
                  [SEQ1]
      [MUT2G]ACAAGGCTCACGCTGGCCATCTCAATGGAGTTTATTACCAAGGTGGCACTTACTCAAAAG
1141  ---------+---------+---------+---------+---------+---------+  1200
      TGTTCCGAGTGCGACCGGTAGAGTTACCTCAAATAATGGTTCCACCGTGAATGAGTTTTC

LysAlaHisAlaGlyHisLeuAsnGlyValTyrTyrGlnGlyGlyThrTyrSerLysAla -
                                                                [SEQ2]
      CATCTACTCCTAATGGTTATGATAATGGCATTATTTGGGCCACTTGGAAAACCCGGTGGT
1201  ---------+---------+---------+---------+---------+---------+  1260
      GTAGATGAGGATTACCAATACTATTACCGTAATAAACCCGGTGAACCTTTTGGGCCACCA
                  [SEQ3]
                  SerThrProAsnGlyTyrAspAsnGlyIleIleTrpAlaThrTrpLysThrArgTrpTyr -
      ATTCCATGAAGAAAACCACTATGAAGATAATCCCATTCAACAGACTCACAATTGGAGAAG
1261  ---------+---------+---------+---------+---------+---------+  1320
      TAAGGTACTTCTTTTGGTGATACTTCTATTAGGGTAAGTTGTCTGAGTGTTAACCTCTTC
```

FIG. 7B

```
           SerMetLysLysThrThrMetLysIleIleProPheAsnArgLeuThrIleGlyGluGly -
     GACAGCAACACCACCTGGGGGGAGCCAAACAGGCTGGAGACGTTTAAAAGACCGTTTCAA
1321 ---------+---------+---------+---------+---------+---------+ 1380
     CTGTCGTTGTGGTGGACCCCCCTCGGTTTGTCCGACCTCTGCAAATTTTCTGGCAAAGTT

GlnGlnHisHisLeuGlyGlyAlaLysGlnAlaGlyAspValEnd
     AAGAGATTTACTTTTTTAAAGGACTTTATCTGAACAGAGAGATATAATGGGCGGCCGC
1381 ---------+---------+---------+---------+---------+-------   1437
     TTCTCTAAATGAAAAAATTTCCTGAAATAGACTTGTCTCTCTATATTACCCGCCGGCG
```

FIG. 7C

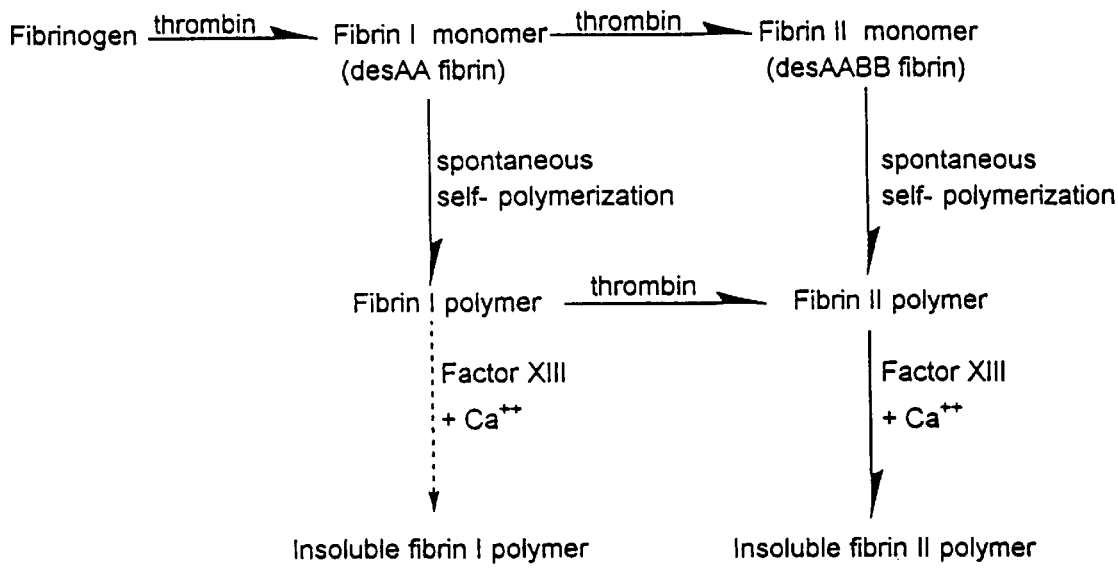

FIG. 8

RECOMBINANT FIBRIN CHAINS, FIBRIN AND FIBRIN-HOMOLOGS

This application is a continuation-in-part of application Ser. No. 08/236,979 filed May 2, 1994, now abandoned.

The invention is directed to fibrin materials for use in fibrin compositions and methods that avoid the need to use thrombin as an activating agent.

DEFINITIONS

The terms listed below, as used herein, will have the meaning indicated. Unless indicated otherwise, the terms "peptide", "polypeptide" and "protein" are used interchangably mean two or more amino acids linked by a peptide bond.

| Term | Definition |
|---|---|
| α-chain | = The alpha-chain is one of the three component polypeptide chains of fibrin. Except for missing the sequence of the N-terminal fibrinopeptide A, the amino acid sequence of the α-chain is generally the same as that of the Aα-chain of fibrinogen. The α-chain is also referred to as fibrin α-chain. |
| Aα-chain | = The α-chain linked with the N-terminal A fibrinopeptide. The Aα-chain is also referred to as the fibrinogen Aα-chain. |
| amino acid numbering and ordering | = All amino acid numbering for fibrin chains is for the human sequences starting from initial methionine of the unprocessed gene product; for non-human sequences, the sequence ranges set forth herein refer to the homologous sequences. For instance, for the human γ-chain, the first amino acid of the processed polypeptide is residue 27, numbered from the N-terminal methionine of unprocessed gene product. For purposes of this application an amino acid is ordered "in front of" or "before" another if it is closer to the N-terminal than the other. |
| β-chain | = The beta-chain is one of the three component polypeptide chains of fibrin. Except for missing the sequence of the N-terminal fibrinopeptide B, the amino acid sequence of the β-chain is generally the same as that of the Bβ-chain of fibrinogen. The β-chain is also referred to as the fibrin β-chain. |
| Bβ-chain | = The β-chain linked with the N-terminal B fibrinopeptide. The Bβ-chain is also referred to as the fibrinogen Bβ-chain. |
| chain | = A component polypeptide of fibrin, fibrin-homolog, fibrinogen or fibrinogen-analog. |
| coiled-coil region | = The regions of fibrin, fibrin-homolog, fibrinogen or fibrinogen-analog connecting the D-domains with the central E-domain are made up of a "coiled-coil" of helical regions, each helical region formed from one of an α-chain, a β-chain, and a γ-chain or a vγ-chain. Together, these helical regions comprise the coiled-coil region. |
| conserved two Cys residues of the C-terminal portion of γ-chain | = The Cys residues generally found in the C-terminal portion of all natural γ-chain sequences. In the human sequence, these are residues 352 and 365. |
| construct | = A nucleotide sequence produced using recombinant DNA technology. |
| crosslinked fibrin polymer | = A fibrin polymer where covalent crosslinks have formed between the polymerized fibrin-related proteins, such as the crosslinks formed by factor XIII. |
| des BB fibrin | = A fibrin that lacks the B fibrinopeptides, but retains the A fibrinopeptides. |
| des BB fibrin monomer | = The individual des BB fibrin units, as contrasted with a fibrin polymer formed with des BB fibrin. |
| extended α-chain or extended β-chain | = An α-chain with an N-terminal extension or a β-chain with an N-terminal extension. |
| fibrin | = One of a number of derivatives of fibrinogen (e.g., fibrin I, fibrin II or des BB fibrin) that can polymerize to form a clot. The derivatives are created by cleaving the A or B fibrinopeptides from fibrinogen. |
| fibrin I | = A fibrin that lacks the A fibrinopeptides but retains the B fibrinopeptides. Fibrin I can polymerize to form a clot. |
| fibrin I monomer | = Since fibrin I is polymerizable, the term "fibrin I monomer" is used to identify the individual fibrin I units. |
| fibrin II | = A fibrin that lacks the A fibrinopeptides and the B fibrinopeptides. Fibrin II can polymerize to form a clot. |
| fibrin II monomer | = Since fibrin II is polymerizable, the term "fibrin II monomer" is used to identify the individual fibrin II units. |
| fibrin chain | = Any of the chains that comprise fibrin monomer, fibrin-homolog or fibrinogen-analog, including α-chain, β-chain, γ-chain or modified γ-chain such as vγ-chain. |
| fibrin chain-precursor | = Precursor of a fibrin chain containing a N-terminal leader peptide that can be cleaved to yield the fibrin chain. A fibrin chain-precursor is a fibrin chain with a specific type of N-terminal extension. |
| fibrin chain with an N-terminal extension | = A fibrin chain linked, at its N-terminal, and via a peptide bond, with an amino acid, peptide or protein. |
| fibrin chain with an N-terminal extension lacking a thrombin recognition sequence | = N-terminal extension to an α-chain, β-chain, γ-chain or modified γ-chain that is not susceptible to thrombin cleavage to generate an α-chain, β-chain, γ-chain or modified γ-chain. |
| fibrin chain with an N-terminal extension that is not adapted for proteolytic processing | = N-terminal extensions to an α-chain, β-chain, γ-chain or modified γ-chain that is not susceptible to proteolytic cleavage to generate an α-chain, β-chains, γ-chain or modified γ-chain. |
| fibrin-homolog | = This differs from fibrin I-, II- or des BB fibrin- monomer, in that modified γ-chains substitute for γ- chains. |
| fibrin-homolog precursor | = A fibrinogen-like molecule comprising one or more fibrin chain precursors and either modified γ-chains or modified γ-chain precursors. A fibrin-homolog precursor contains one or more leader peptides on its constituent chains. The leader peptide(s) can be proteolytically processed in vivo or in vitro from the fibrin-homolog precursor to yield fibrin-homolog. |
| fibrin or fibrinogen-related protein | = A protein related to fibrin or fibrinogen that includes two α-chain homologous polypeptides, two β-chain homologous polypeptides, and two γ-chain or vγ-chain homologous polypeptides. |
| fibrin polymer | = Any composition of fibrin-related proteins that have associated covalently or non-covalently to form a polymer of fibrin-related proteins. |
| fibrin precursor | = Precursor of fibrin comprising one or more fibrin chain precursors. A fibrin precursor contains one or more leader peptides on its constituent chains. The leader peptide(s) can be processed in vivo or in vitro from the fibrin precursor to yield fibrin. |
| fibrin sealant | = A biological adhesive whose effect imitates the final stages of coagulation, thereby resulting in a fibrin clot. Fibrin |

| | | |
|---|---|---|
| | | sealants are useful in surgery to control bleeding or to adhere two tissues to each other. |
| fibrinogen | = | The protein found in the circulatory systems of animals that functions to provide building blocks for forming clots. Fibrinogen contain two Aα-chains, two Bβ-chains and two γ-chains. When fibrinogen is processed to fibrin monomer, the fibrin monomer is capable polymerizing to form clots. |
| fibrinogen-analog | = | A molecule that differs from fibrin in having at least one N-terminal extension to the α-chain or the β-chain, wherein the extension differs from the A or B fibrinopeptide, respectively. When all of the component α- or β-chains have N-terminal extensions, fibrinogen-analogs are generally incapable of self-polymerization. |
| fibrinogen chain | = | A fibrinogen chain is an Aα- or a Bβ-chain. |
| fibrinogen half molecule | = | A fibrinogen half molecule is a precursor to fibrinogen having an Aα-chain, a Bβ-chain and a γ-chain. Two fibrinogen half molecules can form fibrinogen. |
| γ-chain | = | The gamma-chain is one of the three component polypeptides chains of fibrin or fibrinogen. The γ-chain is also referred to as fibrin γ-chain. |
| gene fusion | = | A gene construct comprising a promoter operably linked to the coding sequence of a heterologous gene, wherein the promoter controls the transcription of the coding sequence. |
| genetic-engineering | = | Altering the genetics of a host cell by the introduction and maintenance of nucleotide sequences produced by recombinant DNA methodologies. Genetic engineering can include, but is not limited to, transformation, transduction or transfection of integrative or non-integrative nucleotide sequences that may or may not be capable of autonomous replication in the host cell, as well as methods of producing transgenic multicellular organisms having one or more tissues having cells with altered genetics. |
| heterologous leader peptide | = | A leader peptide that is derived from a protein different than the protein to which said leader peptide is attached. |
| homologous polypeptides | = | Polypeptides having high homology with a significant portion of the sequence of the α-chain, β-chain or γ-chain, for instance with at least about half of one of these chains. |
| in vitro | = | Refers to a process a part or the whole of which does not involve the use of intact cells. For example, in vitro production of fibrin can involve in vitro assembly of fibrin chains that may have been produced by genetically- engineered cells. It can also involve in vitro processing of cellularly produced fibrin chain precursors and in vitro assembly of the resulting fibrin chains into fibrin, or the in vitro assembly of the fibrin chain precursors into a fibrin precursor and the in vitro processing of the fibrin precursor into fibrin. |
| in vivo | = | Refers to a process all of which involves the use of intact cells. For example, in vivo production of fibrin in a genetically-engineered cells involves the cellular expression, processing and assembly of an intact, functional fibrin from expression constructs encoding fibrin chain precursors. |
| leader peptide | = | The polypeptide at the N-terminal of a polypeptide or protein. The leader peptide can be of any size, from a single amino acid to a peptide several amino acids long to an entire protein. As used herein, a leader peptide in all instances has a "pro" function. That is the leader peptide can be specifically and completely removed from the attached polypeptide or protein by, for example, proteolytic processing. In some instance, the leader peptide can additionally have a "pre" function in that it directs cellular compartmentalization or extracellular export of the attached protein. In some instances, the leader peptide can be processed during the membrane translocation step associated with cellular compartmentalization or extracellular export. |
| modified γ-chain or modified gamma-chain | = | Includes all vγ-chains plus chemically modified γ-chains such that, when incorporated into fibrin-homolog, the homolog lacks the ability to self-polymerize but has the ability to form non-covalent bonds with fibrinogen. |
| native fibrin | = | A fibrin derived from an animal. |
| non-covalent bonding | = | Any interaction by which proteins form stable associations, including hydrogen bonds, Van der Waals interactions, hydrophobic interactions, electrostatic interactions and the like. The presence of non-covalent bonds does not exclude the possibility of covalent bonds (i.e., crosslinks). |
| non-covalent fibrin polymer | = | A fibrin polymer wherein the associated fibrin-related proteins are associated through non-covalent bonds. |
| PCR | = | Polymerase chain reaction. |
| recombinant fibrin, fibrin-homolog or fibrinogen-analog | = | Fibrin, fibrin-homolog or fibrinogen-analog produced by genetic-engineering of cells with expression constructs encoding fibrin chains and fibrin chain precursors. |
| RNA | = | Ribonucleic acid. |
| self-polymerizing | = | A population of the same protein molecules in which a first protein molecule bonds covalently or non-covalently with a second protein molecule. |
| stable non-covalent bonds | = | Bonds between fibrin-related proteins that are stable enough to allow the formation of a clot. |
| substantially pure | = | The degree of purity where the compound comprises at least 50% by weight of the material in question. |
| suitable cell | = | A "suitable cell" for the purposes of the present claims is a cell that can process, by proteolytic removal, the selected N-terminal extension encoded by the claimed nucleotide sequence. |
| unfolding amount of denaturant | = | An amount of a composition sufficient to substantially unfold a protein, generally, an amount of denaturant having substantially equivalent polypeptide unfolding activity as 2.5 M urea. |
| vγ-chain or variant γ-chain or variant gamma-chain | = | A variant gamma-chain that contains one or more mutations and/or deletions in the C-terminal region following the coiled-coil forming region such that, when incorporated into fibrin-homolog, the homolog lacks the ability to self-polymerize but has the ability to form non-covalent bonds with fibrinogen. |

Fibrin and Blood Clotting

One mechanism for hemostasis, i.e., prevention of blood loss, of a mammal is the formation of a blood clot. Clot formation in humans occurs by means of a complex cascade of reactions with the final steps being the conversion of fibrinogen by thrombin, calcium ions and activated Factor XIII to form ultimately crosslinked fibrin II polymer, alternatively known as insoluble fibrin II polymer, which is the insoluble fibrin clot.

Fibrinogen represents about 2 to 4 grams/liter of the blood plasma protein and is a complex protein consisting of three pairs of disulfide-linked polypeptide chains designated $(A\alpha)_2$, $(B\beta)_2$, and $\gamma_2$. "A" and "B" represent the two small aminoterminal peptides, known as fibrinopeptide A and fibrinopeptide B, respectively. The six polypeptide chains of fibrinogen are folded into at least three globular domains in a linear disposition, two terminal "D-domains" and a central "E-domain". The E-domain is believed to contain all six N-terminal residues of the polypeptide chains in fibrinogen molecule. Each D-domain contains the C-terminal sequence from one A$\alpha$-chain, one B$\beta$ chain, and one $\gamma$ chain.

The formation of insoluble fibrin clots (i.e. crosslinked fibrin II polymer) is believed to begin with fibrinogen being converted by thrombin to fibrin I monomer. This conversion involves thrombin-mediated cleavage of the 16 amino acid fibrinopeptide A ($G_1$-$R_{16}$) from each the two A$\alpha$-chains of fibrinogen, producing two $\alpha$-chains each with a new N-terminal having the amino acid sequence $G_{17}$-P-R-$V_{20}$-. The fibrin I monomer, it is believed, can spontaneously polymerize with other fibrin I or fibrin II monomers due to intermolecular interactions (i.e., non-covalent bonds) between the E-domain of the converted fibrin monomer, which now has accessible non-covalent bonding sites, and a D-domain of a different fibrin I or fibrin II monomer. Each D-domain of a fibrin monomer carries a polymerization site capable of stably interacting with an E-domain of a fibrin I or fibrin II monomer.

Contacts between the two E-domain polymerization sites of one fibrin I monomer with two complementary D-domain polymerization sites, each from two different fibrin I monomers, are believed to result in linear fibrin fibrils (i.e., polymers) with half staggered overlapping molecular contacts. The fibrin I polymer so formed is sometimes referred to as soluble fibrin I polymer because, by treatment with appropriate chemical means the fibrin I polymer an be depolymerized and reconverted to fibrin I monomers.

The next step in the formation of fibrin clots involves the conversion of fibrin I monomer to fibrin II monomer. This step involves the thrombin-mediated cleavage of the fibrinopeptide B from each of the two B$\beta$-chains of fibrin I. The removal of the 14 amino acid fibrinopeptide B produces $\beta$-chains, each having a N-terminal sequence of G-H-R-. Fibrin II monomers, like fibrin I monomers, can spontaneously polymerize with other fibrin II or fibrin I monomers due to intermolecular interaction sites in the E-domain of one fibrin II monomer, which are made accessible by the cleavage reaction, with the D-domain of another fibrin II or fibrin I monomer. Like fibrin I polymer, fibrin II polymer is also sometimes referred to as soluble fibrin II polymer because by appropriate chemical treatments it can be depolymerized and reconverted to fibrin II monomers. The exposure of the $\beta$-chain N-terminal sequences in the E-domain is critical to fibrin clot formation as it facilitates the activated Factor XIII-mediated covalent crosslinking of adjacent fibrin II monomers in the fibrin II polymer. Although activated Factor XIII is also capable of crosslinking fibrin I monomers in a fibrin polymer, the reaction is less efficient due to the presence of fibrinopeptide B on fibrin I. Crosslinked fibrin II polymer is sometimes referred to as insoluble fibrin II polymer because it cannot be depolymerized and reconverted to fibrin II monomers.

A schematic diagram of the fibrinogen to crosslinked fibrin I polymer and crosslinked fibrin II polymer is shown in FIG. 8.

In addition to thrombin and Factor XIII, calcium ions are believed to be important in the formation of fibrin clots and have a number of important roles. Calcium ions are believed necessary for the activation of prothrombin to thrombin, and since thrombin activates Factor XIII, calcium ions are indirectly necessary for Factor XIII activation. Further, active Factor XIII is believed to be a calcium-dependent enzyme which cannot crosslink fibrin polymers in the absence of calcium ions. Calcium ions also directly bind to polymeric fibrin and change the opacity and mechanical properties of the fibrin polymeric strands. For reviews of the mechanism of blood coagulation and the components of a fibrin clot, see C. M. Jackson, 1980, *Ann. Rev. Biochem.*, 49:765–811, and B. Furie and B. C. Furie, 1988, *Cell*, 53:505–518.

Fibrin Sealants

A fibrin sealant is a biological adhesive whose effect imitates the stages of coagulation to form a fibrin polymer. The sealant can be designed so that the fibrin polymer will be converted to insoluble fibrin polymer. One type of fibrin sealant uses fibrinogen and consists of two components. One component comprises concentrated human fibrinogen, bovine aprotinin and Factor XIII. The second component comprises bovine thrombin and calcium chloride. Application of this type of sealant is generally carried out with a double-barrelled syringe, which permits simultaneous delivery of both components to the desired site of the fibrin clot formation. The mixing of the two components at the target site produces a fibrin clot via the sequence of reactions described above.

The fibrinogen component of this type of fibrin sealant is typically prepared from pooled human plasma. The fibrinogen can be concentrated from the human plasma by cryoprecipitation and precipitation using various reagents, e.g., poly(ethylene glycol), diethyl ether, ethanol, ammonium sulfate or glycine. For reviews of this type of fibrin sealants, see M. Brennan, 1991, *Blood Reviews*, 5:240–244; J. W. Gibble and P. M. Ness, 1990, *Transfusion*, 30:741–747; H. Matras, 1985, *J. Oral Maxillofac Surg.*, 43:605–611 and R. Lerner and N. Binur, 1990, *J. of Surgical Research*, 48:165–181.

A second, newer type of fibrin sealant uses compositions consisting primarily of fibrin I and/or fibrin II monomers. See European Patent Application No. 0 592 242, published April, 1994. In these types of sealants, fibrin I monomers and/or fibrin II monomers and/or desBB fibrin monomers are prepared in advance of sealant application from fibrinogen using an appropriate proteolytic enzyme, such as thrombin. The fibrin monomers are maintained in soluble form using an appropriate buffer. Useful buffers include those that have a low pH and/or a chaotropic agent and preferably have low calcium levels or are calcium-free. The fibrin I monomers, fibrin II monomers or desBB fibrin monomers in such solutions can be converted to fibrin polymers by mixing the solution with a second solution to produce a mixture with conditions that permit the spontaneous polymerization of the fibrin monomers to form a fibrin clot.

Fibrin I, fibrin II and desBB fibrin monomer-based sealants have several advantages over fibrinogen-based sealants. Notably, fibrin monomer-based sealants do not include bovine or human thrombin. The use of such sealants, when the fibrin monomer is prepared from the autologous source (i.e., the patients themselves), introduces no foreign proteins into the recipient and thereby avoids complications arising from immunological reactions and risk of blood borne infections. The fibrin monomer-based sealants can be conveniently prepared. Soluble fibrin polymer can be dissolved using a weak acidic solution and the resulting fibrin monomers lyophilized to fine powders. Such powders can easily be redissolved in a weak acid and induced to repolymerize by the addition of an alkali buffer. Alternatively, the powdered fibrin monomers can be dissolved in a chaotropic solution, e.g., urea, to a very high concentration (>150 mg/ml) and induced to repolymerize by the addition of water.

A further advantage of fibrin monomer-based sealants is that as they generally use autologous components, their use poses a lower risk of exposure to blood-transmitted infectious agents such as hepatitis (including hepatitis B, and non-A, non-B hepatitis) and acquired immune deficiency virus (AIDS). See L. E. Silberstein et al., 1988, *Transfusion*, 28:319–321; K. Laitakari and J. Luotonen, 1989, *Laryngoscope*, 99:974–976 and A. Dresdale et al., 1985, *The Annals of Thoracic Surgery*, 40:385–387. Diseases caused by such agents can be transmitted by conventional fibrinogen-based sealants because the fibrinogen component is typically prepared from pooled human plasma. Moreover, the use of fibrin-based sealants can also avoid the risks associated with the bovine thrombin component of fibrinogen-based sealants. Bovine thrombin preparations can carry the infectious agent bovine spongiform encephalitis (BSE) as well as other viral pathogens of mammals. Also, bovine thrombin is a potent antigen, which can cause adverse immunological reactions in humans. For further discussions of these types of complications that are associated with fibrinogen-based sealants, see D. M. Taylor, 1991, *J. of Hospital Infection*, 18 (Supplement A):141–146 and S. B. Prusiner et al., 1991, *Cornell Vet*, 81:85–96.

Accordingly, there is the need for preparations of fibrin sealants that are free of viral infection and/or allergenic effects. While the use of autologous fibrin in fibrin monomer-based sealants is a solution, its application is unfortunately limited to situations where advanced planning, in the way of collecting and preparing a sufficient amount of autologous fibrin monomer, is possible. However, where advanced planning is not possible, i.e., emergencies, or where only a limited amount of autologous plasma can be set aside, (i.e., neonates), there remains a need for infection-free fibrin monomers that can be used in the preparation of safe and convenient fibrin sealants.

Recombinant Fibrinogen and Fibrin

Genetic engineering offers a way to produce fibrinogen and fibrin monomers in comparatively high yields, in substantially pure form, and in the absence of pathogenic viruses such as hepatitis and HIV. Heterologous expression of fibrinogen and fibrin chains also allows the construction of mutations which can mimic naturally occurring fibrin variants and the isolation and study of these proteins without a need for patients with these rare genetic defects.

Each of the three different polypeptide chains (A$\alpha$, B$\beta$ and $\gamma$) of fibrinogen is coded by a separate gene. The cDNAs for each of these chains have been prepared (Chung et al., 1983, *Ann N.Y. Acad. Sci.*, 408:449–456; Rixen et al., 1983, *Biochemistry*, 22:3237–3244; Chung et al., 1983, *Biochemistry*, 22:3244–3250; Chung et al., 1983, *Biochemistry*, 22:3250–3256) and expressed in procaryotic organisms. Furthermore, each human fibrinogen chain has been introduced separately (Huang et al., 1993, *J. Biol. Chem.*, 268:8919–8926; Roy et al., 1992, *J. Biol. Chem.*, 267:23151–23158; Roy et al., 1991, *J. Biol. Chem.*, 266:4758–4763) or in combination (Hartwig and Danishefsky, 1991, *J. Biol. Chem.*, 266:6578–6585; Huang et al., ibid.; Roy et al., 1991, *J. Biol. Chem.*, 266:4758–4763) into expression plasmids and transfected into eucaryotic cells.

Most of the plasmids used in expressing recombinant human fibrinogen are derived from those constructed by Dr. D. Chung, University of Washington, Seattle and are based on cDNA clones (Rixen et al., 1983, *Biochemistry*, 22:3237–3244; Chung et al., 1983, *Biochemistry*, 22:3244–3250; Chung et al., 1983, *Biochemistry*, 22:3250–3256). The expression of recombinant fibrinogen chains were first achieved in *E.coli* (Bolyard and Lord, 1988, *Gene*, 66:183; Bolyard and Lord, 1989, *Blood*, 73:1202–1206; Lord and Fowlkes, 1989, *Blood*, 73:166–171). The individually expressed chains showed antigenic similarities with fibrinogen and displayed thrombin cleavable sites similar to those found in native fibrinogen (Bolyard and Lord, 1989, *Blood*, 73:1202–1206; Lord and Fowlkes, 1989, *Blood*, 73:166–171). The release of fibrinopeptides A and B was also observed (Bolyard and Lord, 1989, *Blood*, 73:1202–1206; Lord and Fowlkes, 1989, *Blood*, 73:166–171).

Eucaryotic cells carrying appropriate expression plasmids encoding individual fibrinogen chains have been shown to synthesize the encoded fibrinogen chains and to result in the intracellular formation of dimeric chain molecules, e.g. A$\alpha_2$, B$\beta_2$ or $\gamma_2$ dimers (Roy et al., 1990, *J. Biol. Chem.*, 265:6389–6393; Zhang and Redman, 1992, *J. Biol. Chem.*, 267:21727–21732). Furthermore, when appropriate plasmids containing genes encoding for all three human fibrinogen chains are transferred into the same cell, then not only are all three chains expressed but the polypeptide chains associate in pairs and intact fibrinogen is secreted into the surrounding medium (Roy et al., 1991, *J. Biol. Chem.*, 266:4758–4763; Hartwig and Danishefsky, 1991, *J. Biol. Chem.*, 266:6578–6585). Like natural fibrinogen, the secreted recombinant fibrinogen consists of three pairs of non-identical polypeptide chains and is functional in forming fibrin polymers.

Fibrinogen is naturally synthesized by liver, and megakaryocyte cells and transformed liver cells maintained in culture are able to continue fibrinogen synthesis and secretion (See Otto et al., 1987, *J. Cell. Biol.*, 105:1067–1072; Yu et al., 1987, *Thromb. Res.*, 46:281–293; Alving et al., 1982, *Arch. Biochem. Biophys.*, 217:19). One such cell line is the Hep G2 cells (Drs. Knowles and Aden, Wister Institute, Philadelphia). This line synthesizes an excess of A$\alpha$- and $\gamma$-chains over the B$\beta$-chains resulting in non-productive dimeric complexes of A$\alpha$- and $\gamma$-chains (e.g., A$\alpha_2\gamma_2$). The introduction of an additional expression vector encoding B$\beta$-chains resulted in the formation of trimeric complexes (A$\alpha$B$\beta\gamma$) which adopt the correct folding and intrachain disulfide bonding patterns (Roy et al., 1990, *J. Biol. Chem.*, 265:6389–6393). The mechanism of this folding is unknown and may involve ancillary proteins and enzymes (Roy et al., 1992, *J. Biol. Chem.*, 267:23151–23158). These studies demonstrated not only the correct transcription of B$\beta$ cDNA but also that the excess B$\beta$-chain enhanced the assembly and secretion of intact fibrinogen.

In Hep G2 cells, the A$\alpha$B$\beta\gamma$ trimeric complexes associate in pairs to form intact fibrinogen molecules, which become glycosylated and are actively secreted from the cell (Huang et al., 1993, *J. Biol. Chem.*, 268:8919–8926). Indeed only correctly assembled fibrinogen molecules are secreted. Thus, Hep G2 cells have the synthetic and secretory apparatus for the assembly of fibrinogen.

Subsequent experiments have introduced fibrinogen chain encoding cDNA plasmids into eukaryotic cells that do not normally synthesize fibrinogen. These experiments successfully produced functional fibrinogen, demonstrating that the factors needed for fibrinogen assembly and secretion are not unique to liver-derived cells like Hep G2. Eucaryotic cells known to be capable of assembling and secreting recombinant fibrinogen include baby hamster kidney cells (BHK), COS cells and Chinese hamster ovary cells (CHO) (Roy et al., 1991, *J. Biol. Chem.*, 266:4758–4763; Hartwig and Danishefsky, 1991, *The Journal of Biol. Chem.*, 266:6578–6585; Farrell et al., 1991, *Biochemistry*, 30:9414–9420).

Intact functional fibrinogen secreted by stably transformed eukaryotic cells results in the accumulation of fibrinogen levels of around 1–2 µg/ml. Methods are known for increasing the output of recombinant proteins from transfected cells like CHO cells such that the expression levels can approach a thousand fold the basal secretory level.

Despite such successful demonstrations, recombinant fibrinogen does not provide a completely satisfactory solution to the production of fibrin sealants that are safe from viral contamination or adverse allergenic effects. For, in as much a the use of recombinant fibrinogen in fibrin sealant still requires processing by animal produced thrombin, significant concerns remain over viral contamination and allergic reactions stemming from the thrombin component of such fibrinogen-based sealants.

Expression of Heterologous Proteins in Yeast and Aspergillus

With the advent of recombinant DNA technology, efforts have been made to express heterologous DNA in a variety of prokaryotic and eukaryotic systems. Two such systems are yeast and the filamentous fungi Aspergillus.

Yeast and other fungi such as Aspergillus have a number of advantages over bacteria and other eukaryotes as a system for the production of polypeptides or proteins encoded by recombinant DNA. Yeast and other fungi have been extensively used in large scale fermentations, so the technologies for fermenting yeast and other fungi are well known and numerous yeast or other fungal hosts and expression vectors have been developed. See Kingsman et al., 1985, *Biotechnology and Genet. Engineering Rev.*, 3:337–416 (Saccharomyces yeasts); Reiser et al., 1990, *Adv. Biochem. Engineering and Biotechnol.*, 43:75–102; (non-Saccharomyces yeasts); Sanders et al., 1989, *Trends. Biotechnol.* 7:283–287, Jeenes et al., (1991) *Biotechnol. Genet. Eng. Reve.*, 9:327–367, van den Hondel et al., (1991) More Gene Manipulations in Fungi, Bennett and Lasure, Eds., pp. 396–428. Additionally, yeast and other fungi can be grown to higher densities than bacteria and many other types of eukaryotic cells, and are readily adaptable to continuous fermentation processing. Since yeast and other fungi are eukaryotic organisms, they will generally exhibit the same or similar codon preferences as higher organisms. Further, they naturally secrete a wide range of glycoproteins which makes these systems especially attractive for the production of extracellular eukaryotic glycoproteins. The secretion may result from the ability of yeast and other fungi to correctly recognize and process heterologous leader peptides as well as the availability of a wide range of cloned homologous leader peptides that can be used to construct secretable fusion proteins. See Cullen et al., 1987, *Bio/Technology*, 5:369–376; van Hartingsveldt et al., 1991, *Proceedings of the 6th International Symposium on the Genetics of industrial Microorganisms* (Strasbourg), 107–116; Kingsman et al., ibid; Reiser et al., ibid; Ward et al., 1990, *Bio/Technology*, 8:435–440. Yeast and other fungi also correctly perform most eukaryotic post-translational modifications, such as N-terminal processing and glycosylation. See Kingsman et al., ibid; Reiser et al., ibid; Van Brunt, 1988, *Biotechnol.* 4:1057–1062.

Numerous heterologous proteins have been successfully expressed and secreted in the yeast Saccharomyces. Examples include interferon (Hitzeman and Leung, U.S. Pat. No. 4,775,622, issued Oct. 4, 1988; Hitzeman et al., Canadian Patent No. 1,205,026, issued May 27, 1986; Hitzeman et al., 1981, *Nature* (London) 293: 717); platelet derived growth factor (Murray et al., U.S. Pat. No. 4,801,542, issued Jan. 31, 1989); glucagon (Norris et al., U.S. Pat. No. 4,826,763, issued May, 1989). See also Reiser et al. for heterologous protein produced in yeast other than Saccharomyces.

Similarly, numerous heterologous proteins have also been successfully expressed and secreted in fungi. Examples include porcine pancreatic prophospholipase A2 (Roberts et al., 1992, *Gene* 122:155–161); hen egg-white lysozyme (Jeenes et al., 1993, *FEBS Microbiol.* 107:267–272); human lactoferrin (Ward et al., 1992, *Gene* 122:219–223); human lysozyme (Tsuchiya et al., 1992, *Appl. Microl. Biotechnol.* 38:109–114); human interferon (Gwynne et al., 1987, *Biotechnol.* 5:713–719); bovine chymosin (Cullen et al., 1987, *Biotechnol.* 5:369–376); human tissue plasmogen activator (Upshall et al., 1987, *Biotechnol.* 5:1031–1034); see also Jeenes et al., 1991, *Biotechnol. Genet. Eng. Rev.*, 9:327–367 and van den Hondel et al., 1991, *More Gene Manipulations in Fungi*, Bennett and Lasure, Eds., pp. 396–428–428.

SUMMARY OF THE INVENTION

The present invention generally relates to recombinant fibrin chains, fibrin monomers, fibrin-homologs and fibrinogen-analogs. The recombinant fibrin chains are useful in the production of fibrin chain-derived factors and in the production of fibrin monomers, fibrin-homologs and fibrinogen-analogs, which in turn are useful in the preparation of safe and convenient surgical adhesives and sealants. The invention provides for the production of recombinant fibrin chains as well as fibrin I, desBB fibrin and fibrin II monomers, and useful derivatives that do not require prior enzymatic processing to form fibrin-like polymers.

The invention is directed, in one aspect, to a method of preparing fibrin I, fibrin II and desBB fibrin monomers from preparations comprising, for instance, (a) alpha-fibrin chain (α-chain), fibrin beta-chain (β-chain) and gamma-fibrin chain (γ-chain), (b) fibrin alpha-chain (α-chain), fibrinogen B-beta-chain (Bβ-chain) and gamma-fibrin chain (γ-chain), or (c) fibrinogen A-alpha-chain (Aα-chain), fibrin beta-chain (β-chain) and fibrin gamma-chain (γ-chain). In one case, the fibrin monomers are prepared from the component polypeptide chains in vitro; otherwise, the fibrin monomers are prepared in vivo in an organism containing DNA constructs that direct the synthesis of one of the combinations (a)–(c) of fibrin chains identified above. In another aspect, the invention is directed to fibrin I, desBB-fibrin and fibrin II monomer compositions that are essentially free of at least one of fibrinogen half-molecule, fibrinogen, fibrinogen Aα-chain, fibrinogen Bβ-chain, fibrinopeptide A and fibrinopeptide B.

In yet another aspect, the invention is directed to fibrin-homologs lacking the A and/or the B fibrinopeptides wherein the gamma chain is a variant gamma chain that is altered such that the fibrin-homolog cannot self-polymerize, but can polymerize with fibrinogen. Preferably, the variant γ-chain is altered in the globular region situated in the D-domain such that the globular region cannot form the stable intramolecular non-covalent bonds with the E domain of adjacent fibrin monomers (which interactions are involved in fibrin polymerization). In still another embodiment, the invention is directed to methods of forming fibrin sealants by mixing compositions comprising fibrin-homolog with fibrin-related compositions such as fibrin I monomer, fibrin II monomer, desBB fibrin monomer, fibrinogen or fibrinogen analog compositions. The invention is further directed to nucleotide sequences encoding N-terminal extensions, including export leader sequences derived from either a fibrin leader sequence or a leader sequence from another export protein, wherein the N-terminal extension-encoding sequence is coupled to the nucleotide sequence of the α-chain or the β-chain. Also, the invention is directed to γ-chain analogs that lack the structure required for D-domain interaction with E domains.

One aspect of the present invention relates to the use of novel fibrin chain-precursors and nucleic acid sequences encoding such precursors to produce fibrin chains and fibrin I, fibrin II and desBB fibrin monomers.

A fibrin chain precursor of the invention comprises a heterologous leader peptide fused to the N-terminal of an α-, β- γ- or vγ-chain. The invention provides four different classes of fibrin chain precursors: α-chain precursors, β-chain precursors, γ-chain precursors and variant fibrin gamma-chain (vγ-chain or variant γ-chain) precursors. According to the present invention, the leader peptide functions as a "pro" sequence that can be cleaved from a "free" fibrin chain precursor or from a fibrin chain precursor that has been assembled into a fibrin precursor to yield a fibrin chain or fibrin, respectively. The leader peptide can additionally function as a "pre" sequence providing for cellular localization or extracellular export of the fibrin chain precursor or fibrin precursor containing the leader peptide. The N-terminal extensions described above may also function as "pre" sequences.

The invention provides for nucleotide sequences encoding the novel fibrin chains of the invention and expression constructs comprising the coding sequences operably linked to promoters. According to the invention, cellular expression of the constructs can be used to produce individual fibrin chains. Further, simultaneous cellular expression of particular combinations of the constructs can be used to produce fibrin. Fibrin monomer-producing combinations may have one each of the following expression constructs: 1) an α-chain construct or an Aα-chain construct; 2) a β-chain construct (for the production of fibrin 11) or a Bβ-chain construct (for the production of fibrin l); and 3) a γ-chain construct or a vγ-chain construct, all of which constructs may encode fibrin chain precursors or other N-terminal extensions to the fibrin chains.

Another aspect of the present invention relates to novel fibrin-homologs that have structures and properties similar to those of fibrin, and to the use of nucleic acid sequences encoding fibrin chain precursors and novel variant γ-chain precursors to produce the fibrin-homologs. The fibrin-homolog of the invention is incapable of reacting with itself to form homogeneous polymers, but can under appropriate conditions form heterogeneous polymers comprising, for example, the fibrin-homolog and fibrin monomer or fibrinogen.

A novel fibrin-homolog of the invention may comprise one pair each of the following chains: 1) α-chain or Aα-chain (in a desBB fibrin-homolog); 2) β-chain (in a fibrin II-homolog) or Bβ-chain (in a fibrin I-homolog); and 3) a variant γ-chain. A variant γ-chain of the invention contains one or more mutations or deletions in the region of the γ-chain which, when the vγ-chain is assembled into a fibrin-homolog, forms a globular structure in the D-domain. These mutations or deletions diminish or abolish the homolog's D-domains' ability to non-covalent bond with the E-domains of other fibrin or fibrin-homolog monomers. Such mutations, however, do not affect the fibrin-homolog's ability to participate in intermolecular non-covalent bonding with other fibrin or fibrinogen monomers through its E-domain. Thus, the fibrin-homologs can be used to form heterogeneous polymers useful as surgical adhesives or sealants by combining them with fibrinogen, fibrin monomer or other types of fibrin-related proteins that have functional D-domains.

Like the fibrin chain precursors, the novel variant γ-chain precursors of the invention may, in particular embodiments, contain a pro or a prepro leader peptide. The invention provides that the leader peptide may be processed post-translationally, before or after assembly of the vγ-chain precursor into a fibrin-homolog or a fibrin-homolog precursor.

The invention provides for nucleotide sequences encoding vγ-chains and expression constructs comprising these coding sequences operably linked to promoters. According to the invention, simultaneous cellular expression of particular combinations of constructs encoding vγ-chains, fibrinogen chains, and fibrin chain-precursors can be used to produce the desired fibrin-homolog. Useful combinations of constructs include those having at least one each of the following expression constructs: 1) a construct for forming an α-chain or an α-chain with an N-terminal extension; 2) a construct for forming a β-chain or a β-chain with an N-terminal extension; and 3) a construct forming a vγ-chain or a vγ-chain with an N-terminal extension.

An additional aspect of the present invention relates to novel means of producing recombinant fibrin chains, fibrin and fibrin-homologs. In particular, the present invention provides for cell culture systems that express fibrin or fibrin chain precursors, that express recombinant genes for fibrin chain precursors to produce fibrin chains, and that express, process and assemble fibrin and fibrin-homologs. The present invention also provides for methods of in vitro processing of fibrin chain precursors to form fibrin chains and methods for in vitro assembly of the fibrin chains to form fibrin and fibrin-homologs.

Fibrin chains produced by methods of the present invention can be used as sources of substantially pure starting material for the production of fibrin-derived factors that regulate angiogenesis, platelet aggregation, etc. Fibrin and fibrin-homologs produced by methods of the present invention can be used as components of fibrin-monomer based surgical sealants.

DESCRIPTIONS OF THE FIGURES

FIG. 1. The synthetic leader sequence used in the construction of an α-chain precursor construct (SEQ ID NO: 1 for the first sequence, and SEQ ID NO:2 for the complementary sequence). (See Section 1).

FIG. 2. The synthetic leader sequence used in the construction of a β-chain precursor construct (SEQ ID NO: 3 for the first sequence, and SEQ ID NO:4 for the complementary sequence). (See Section 2).

FIG. 3. The synthetic 3' end fragment used in construction of gamma fibrin chain construct (SEQ ID NO: 5 for the first sequence, and SEQ ID NO:6 for the complementary sequence). (See Section 3).

FIG. 4. The synthetic KpnI/SalI adaptor used in the construction of gamma fibrin chain construct (SEQ ID NO:7). (See Section 3).

FIG. 5. The oligonucleotide used in construction of recombinant fibrin chains (SEQ ID NOS:8–25 correspond to the first 18 sequences of the Figure, respectively). (See Section 1).

FIG. 6. The schematic of the expression cassette of pIGF fusion vector. (See Section 6).

FIG. 7. Partial nucleotide and amino acid sequences (SEQ ID NOS: 26 and 27, respectively) of human γ-chain. The locations of mutagenesis primers MUT1G and MUT2G and sequencing primers PCRY and PCRX are indicated. (See Section 4).

FIG. 8. A schematic of the conversion pathway from fibrinogen to crosslinked fibrin-II polymer.

DETAILED DESCRIPTION OF THE INVENTION

Figure 6:
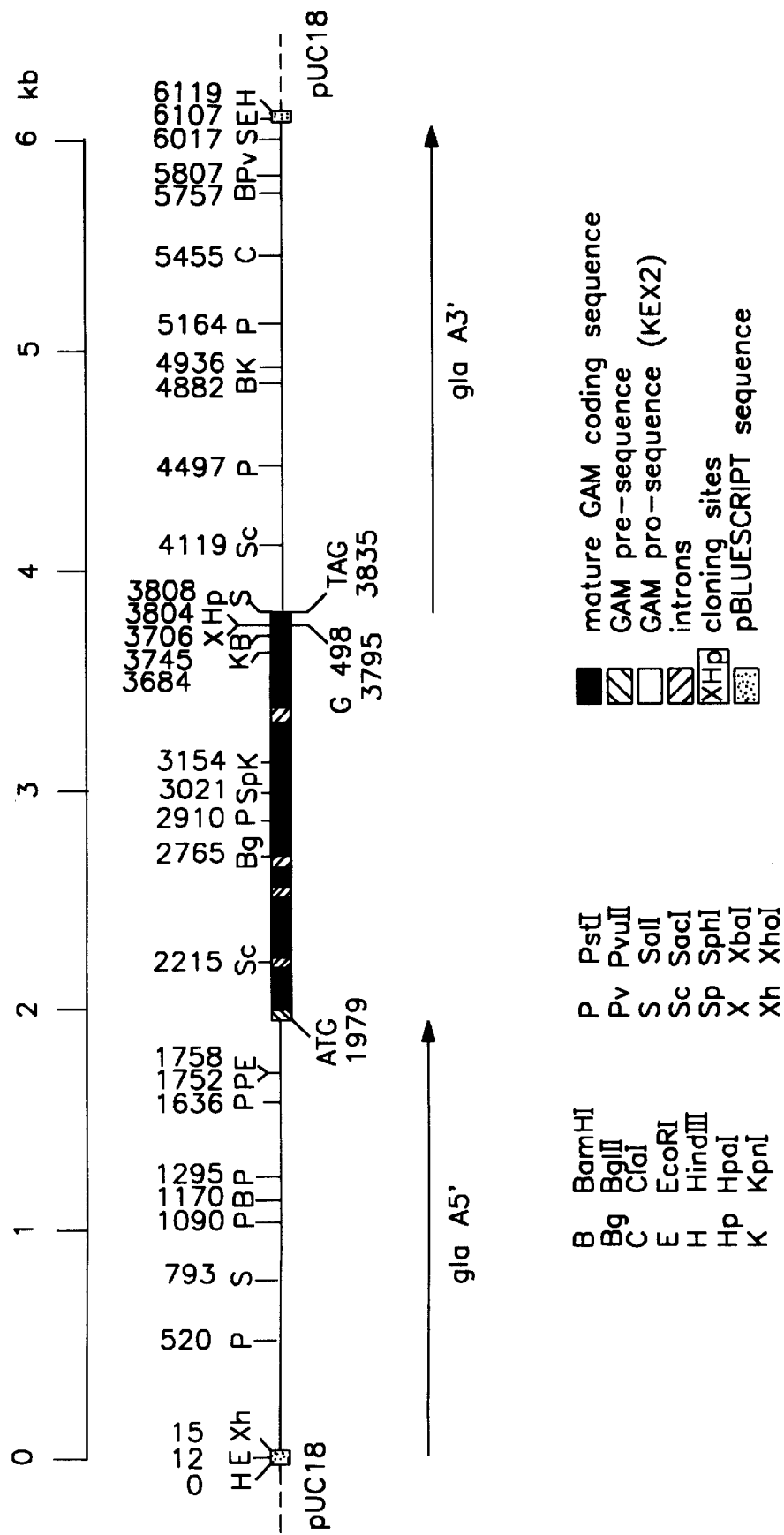

The present invention relates to recombinant fibrin chains, fibrin and fibrin-homologs. Recombinant fibrin chains are useful sources of fibrin-derived regulatory factors. Recombinant fibrin and fibrin-homologs are useful as functional components of safe and convenient fibrin sealants. The invention provides for the production of substantially pure fibrin chains, fibrin, fibrin-homologs, fibrinogen-analogs and their precursors after genetic-engineering of host cells with expression constructs encoding fibrinogen chains, fibrin chains, fibrin chain precursors and fibrin chains with N-terminal extensions.

The recombinant fibrin monomer and fibrin-homologs, of the invention have secondary and tertiary structures that are similar, if not identical, to those of natural fibrin produced by thrombin processing of fibrinogen, particularly in the coiled-coil regions and the E-domains. Like natural fibrin monomer, the recombinant fibrin monomers and fibrin-homologs of the invention each comprise three pairs of non-identical polypeptides covalently linked by intrachain and interchain disulfide bonds. The non-identical polypeptides that form recombinant fibrin are fibrin α-, β- and γ-chains or their precursors. The non-identical polypeptides that form recombinant fibrin-homologs are fibrin α-, β- and modified γ-chains such as vγ-chains or their precursors. In particular instances, fibrinogen Bβ-chains may substitute for β-chains, for instance to form fibrin I and fibrin I-homologs or Aα-chains may substitute for α-chains, for instance to form desB, fibrin-homologs. Additionally, the α-chains or β-chains can have N-terminal extensions that differ from the respective A or B fibrinopeptides. These N-terminally extended chains can be used to form molecules that have sequences that block or inhibit polymerization, as A and B fibrinopeptides function. These molecules are fibrinogen-analogs. In some embodiments, these extensions are cleavable to generate from fibrinogen-analogs, fibrin I, fibrin II or desBB fibrin monomers (in which cases, the fibrinogen-analogs are fibrin precursors). The recombinant fibrin monomers, fibrin-homologs and fibrinogen-analogs of the invention can, without further protein processing and under the appropriate conditions, form homogeneous or heterogenous fibrin or fibrin-like polymers that can be used as the functional component of surgical sealants.

More particularly, one aspect of the present invention pertains to the use of novel fibrin chain precursors and nucleotide sequences encoding such precursors to produce fibrin chains. The novel fibrin chain precursors comprise a heterologous leader peptide fused to the N-terminal of a α-chain, β-chain, γ-chain or vγ-chain. The leader peptide can function as a pro sequence that can be completely and specifically processed from the fibrin chain precursor or the fibrin or fibrin-homolog precursors containing a fibrin chain precursor. In preferred embodiments, the leader peptide may additionally function as a "pre" sequence that directs the cellular compartmentalization or extracellular export of the fibrin chain-precursor or the precursors of fibrin and fibrin-homolog containing the leader peptide. The nucleotide sequences provided by the invention encode novel fibrin chain precursors. The invention also provides for expression constructs that operably linked the fibrin chain precursor coding sequences with promoters that regulate the expression of the coding sequences in host cells.

Another aspect of the present invention relates to fibrin-homologs that have structures and properties similar to those of fibrin, and to the use of novel variant γ-chains or their precursors and nucleic acid sequences encoding such chains and precursors to produce the fibrin-homologs. The variant γ-chains of the invention are mutant γ-chains, whose incorporation into a fibrin molecule (thereby forming a fibrin-homolog molecule) abolishes the ability of the homolog to self-polymerization, but allow the homolog to form non-covalent bonds with fibrinogen. Preferably the two D-domains of the homolog lack the ability to form stable intermolecular non-covalent bonds with the E-domains of other fibrin or fibrin-homolog molecules. Even though the fibrin-homolog of the invention has an activated E-domain (i.e., an E-domain from which the A or B fibrinopeptides are removed), the homolog's loss of D-domain function prevents it from forming a homogeneous polymer. However, such homologs can, when combined with fibrin, fibrinogen or fibrin-homologs that have functional D-domains, form heterogeneous polymers that are useful as surgical sealants. A novel variant γ-chain of the invention has one or more mutations, substitutions and/or deletions in the sequence to the C-terminal side of the coiled-coil-forming sequence. In another embodiment, the variant γ-chain has one or more mutations, substitutions and/or deletions in the sequence from about the first of the C-terminal pair of conserved Cys resides to the C-terminal. In yet another embodiment, the variant γ-chain has one or more mutations, substitutions and/or deletions of the cystine residues that form the C-terminal distal intramolecular disulfide bond. Other variant γ-chains of the invention have other mutations that disrupt the structure of the γ-chain globular domains or delete sequence from the globular domains such that they cannot form stable non-covalent bonds with E-domains.

Yet another aspect of the invention relates to fibrin-related mix polymers comprising (1) a fibrin-homolog comprising a modified γ-chain (which could be a variant γ-chain) and (2) a fibrinogen, fibrinogen-analog or fibrin monomer composition, wherein the fibrin-homolog is non-covalently bonded to the fibrin-related protein of the second composition. Preferably, the fibrin-related protein of the second composition cannot self-polymerize. The invention also provides kits for forming surgical sealants comprising, separately, these two compositions that can form a mix polymer.

Another aspect of the present invention relates to means of producing recombinant fibrin chains, fibrin monomers, fibrin-homologs and fibrinogen analogs. In particular, the present invention provides for host cell systems that have been engineered with the nucleotide sequences and constructs of the invention and correctly express, process and assemble fibrin chain precursors, fibrin chains, fibrin, fibrin-homologs or fibrinogen-analogs. Useful host cells for the expression of the polypeptide and protein molecules of the invention include, but are not limited to, mammalian cells such as baby hamster kidney (BHK) cells, COS cell, Chinese hamster ovary (CHO) cells, liver derived Hep cells; fungal cells such as those from the Saccharomyces genus and Aspergillus genus; as well as bacterial, insect and plant cells.

In some embodiments, the synthesis of one or more of the constituent chains of recombinant fibrin monomer, fibrin-homolog and fibrin-analog is inducible. In other embodiments, the processing of the leader peptide on the precursors of fibrin-chains, fibrin or fibrin-homologs is inducible. In preferred embodiments, the host cells synthesize and export the recombinant fibrin chain, fibrin, fibrin-homologs or their precursors. In particularly preferred embodiments, the host cells synthesize and export the recombinant fibrin, fibrin-homolog or their precursors in low pH media, such as a medium having a pH between about 3.0 and about 5.0, that inhibits polymerization of the exported fibrin or fibrin-homolog. Preferably, the medium has a pH between about 4.0 and about 4.8. Examples of suitable organisms include *Aspergillus flavius, A. niger, A. nidulans*, and *A. oryzae*. The invention also provides for the production of fibrin and fibrin-homologs by in vitro processing of fibrin chain precursors to fibrin chains and the in vitro assembly of the fibrin chains to fibrin and fibrin-homologs Preferably, the proteins or nucleic acids of the invention are at least about 60% pure with respect to macromolecules, more preferably 80% pure, yet more preferably 95% pure.

For clarity of disclosure, and not by the way of limitation, the detailed description of the invention is divided into the following subsections:
1. Fibrin chains, fibrin chain precursors, fibrin and fibrin-homologs;
2. Nucleotide sequences encoding fibrin chains precursors, fibrin chains an fibrinogen chains;
3. Nucleotide sequence encoding variant γ-chains;
4. Expression of fibrin chains, fibrin chains precursors and fibrinogen chains;
5. Identification and, purification of the expressed gene products;
6. Antibodies to fibrin chains;
7. In vitro assembly of fibrin, fibrin homologs, and their precursors;
8. Uses for the recombinant fibrin chains, fibrin and fibrin-homologs;
9. Examples.

1. FIBRIN CHAINS, FIBRIN CHAIN PRECURSORS, FIBRIN AND FIBRIN HOMOLOGS

Fibrin monomer and fibrin-homolog are complex proteins, each consisting of three pairs of non-identical polypeptides covalently linked by intrachain and interchain disulfide bonds. Three different types of fibrin monomer are possible, fibrin I, fibrin II and des BB fibrin monomer. In fibrin I monomer, the three pairs of non-identical polypeptides are: 1) α-chain; 2) fibrinogen Bβ-chain; and 3) γ-chain. In fibrin II monomer, the three pairs of non-identical polypeptides are: 1) α-chain; 2) β-chain; and 3) γ-chain. In des BB fibrin monomer, the three pairs of non-identical polypeptides are: 1) fibrinogen Aα-chain; 2) β-chain; and 3) γ-chain.

Paralleling the three different types of fibrin monomer recited above, different types of fibrin-homolog are possible, including fibrin I-homolog, fibrin II-homolog and des BB fibrin-homolog. The polypeptide compositions of these three types of fibrin-homolog are identical to those of the three different fibrin monomers, except that in each type, modified γ-chains substitute for γ-chains. For example, a fibrin I-homolog can be the following three pairs of non-identical polypeptides: 1) fibrin α-chain, 2) fibrinogen Bβ-chain, and 3) vγ-chain.

A fibrin chain of the invention can be any fibrin chain from a fibrin capable of forming a fibrin clot. Similarly, a fibrinogen chain of the invention can be any fibrinogen chain that can be processed by thrombin to produce a fibrin chain. The preferred chains are those of human fibrin chains and fibrinogen chains. For the nucleotide sequence and the deduced amino acid sequences of human fibrinogen chains, see Rixon et al., 1983, *Biochemistry*, 22:3237–3244; Chung et al., 1983, *Biochemistry*, 22:3244–3250; Chung et al., 1983, *Biochemistry*, 22:3250–3256.

A variant γ-fibrin (vγ-fibrin) chain is a γ-fibrin chain with one or more mutations or deletions in its amino acid sequence. The mutation can be any that disrupts the formation of non-covalent bonds between a fibrin-homologs formed with the vγ-fibrin chain such that the fibrin-homolog cannot self-polymerize. Preferably, the fibrin-homolog can form non-covalent bonds with fibrinogen or another fibrin-related protein. Preferably, the mutations or deletions disrupt the D-domain to E-domain inter-fibrin non-covalent bonding function of the fibrin formed with the vγ-fibrin chain. Preferred mutations or deletions are those that affect the inter-fibrin non-covalent bonding function of the D-domains. Particularly preferred are mutations that disrupt the γ-chain's N-terminal-distal intrachain disulfide bond. Most preferred are mutations of cystine residues that form the disulfide bond, i.e., Cys352 or Cys365 of the human γ-chain or their equivalent in other γ-chains. These mutations can include a missense or an in-frame deletion removing either cystine residue.

To construct non-naturally occurring γ-chain-encoding nucleic acids, the native sequences can be used as a starting point and modified to suit particular needs. For instance, the sequences can be mutated to incorporate useful restriction sites. See Maniatis et al. *Molecular Cloning, a Laboratory Manual* (Cold Spring Harbor Press, 1989). Such restriction sites can be used to create "cassettes", or regions of nucleic acid sequence that are facilely substituted using restriction enzymes and ligation reactions. The cassettes can be used to substitute synthetic sequences encoding mutated γ-chain amino acid sequences. Alternately, the γ-chain-encoding sequence can be substantially or fully synthetic. See, for example, Goeddel et al., *Proc. Natl. Acad. Sci. USA*, 76, 106–110, 1979. For recombinant expression purposes, codon usage preferences for the organism in which such a nucleic acid is to be expressed are advantageously considered in designing a synthetic fibrin chain-encoding nucleic acid.

Deletional or mutational methods of producing recombinant proteins that retain a given activity are well known. Thus, the fibrin-homologs of the present invention encompass analogs of fibrin that have the capacity to polymerize with fibrinogen. These analogs preferably retain all of the sequence of the γ-chain that forms the coiled-coil region of the fibrin molecule. Preferably, the γ-chains will be substantially identical to native γ-chains in all but about the 272 C-terminal amino acid residues, more preferably in all but about the 150 C-terminal amino acid residues, yet more preferably in all but about the 100 C-terminal residues, still more preferably in all but about the 83 C-terminal amino acid residues.

Preferably, the amount of native sequence to be retained will be sufficient to preserve in a fibrin-homolog containing the deleted or mutated γ-chain substantially all of the ability of a native fibrin to form non-covalent bonds with fibrinogen. The retained native sequence will preferably be sufficient to preserve in the fibrin-homolog the ability to form a clot with fibrinogen. The exact boundaries of the sequence that can be removed or mutated to satisfy these criteria can be determined using gene expression methods well known in the art. For instance, the nucleic acid encoding a putative minimal sequence for satisfying these criteria can be expressed and folded into fibrin-homolog using the methods described below, and the ability of the resulting fibrin-homolog to interact with fibrinogen can be tested.

Those of ordinary skill will recognize that all of the fibrin chains described herein, including the deleted γ-chains discussed above, can be mutated to some degree without substantially interfering with the functions described herein or otherwise associated with the respective fibrin chain. Preferably, such chains will have at least about 90% homology, preferably at least about 95%, more preferably at least about 98%, still more preferably at least about 99%, to a native fibrin chain.

Mutational and deletional approaches can be applied to all of the nucleic acid sequences of the invention that express fibrin chains. As discussed above, conservative mutations are preferred. Such conservative mutations include mutations that switch one amino acid for another within one of the following groups:

1. Small aliphatic, nonpolar or slightly polar residues: Ala, Ser, Thr, Pro and Gly;
2. Polar, negatively charged residues and their amides;
3. Polar, positively charged residues;
4. Large aliphatic, nonpolar residues: Met, Leu, Ile, Val and Cys; and
5. Aromatic residues.

A preferred listing of conservative substitutions is the following:

| Original Residue | Substitution |
| --- | --- |
| Ala | Gly, Ser |
| Arg | Lys |
| Asn | Gln, His |
| Asp | Glu |
| Cys | Ser |
| Gln | Asn |
| Glu | Asp |
| Gly | Ala, Pro |
| His | Asn, Gln |
| Ile | Leu, Val |
| Leu | Ile, Val |
| Lys | Arg, Gln, Glu |
| Met | Leu, Tyr, Ile |
| Phe | Met, Leu, Tyr |
| Ser | Thr |
| Thr | Ser |
| Trp | Tyr |
| Tyr | Trp, Phe |
| Val | Ile, Leu |

The types of substitutions selected can be based on the analysis of the frequencies of amino acid substitutions between homologous proteins of different species developed by Schulz et al., *Principles of Protein Structure*, Springer-Verlag, 1978, on the analyses of structure-forming potentials developed by Chou and Fasman, *Biochemistry* 13, 211, 1974 and *Adv. Enzymol*, 47, 45–149, 1978, and on the analysis of hydrophobicity patterns in proteins developed by Eisenberg et al., *Proc. Natl. Acad. Sci. USA* 81, 140–144, 1984; Kyte & Doolittle; *J. Molec. Biol.* 157, 105–132, 1981, and Goldman et al., *Ann. Rev. Biophys. Chem.* 15, 321–353, 1986.

A fibrin chain precursor of the invention consists of a heterologous leader peptide fused to the N-terminal of a fibrin chain. The leader peptide can comprise multiple distinct sequences and have multiple functions. The function of the leader peptide is to enable specific proteolytic cleavage of the fibrin chain precursor at the fusion junction between the leader peptide and the fibrin chain in order to release the fibrin chain with the correct N-terminal sequence. The invention also encompasses fibrin α- and β-chains with N-terminal polypeptide extensions that differ from the A and B fibrinopeptides, respectively. These extended chains can lack thrombin recognition sequences and may or may not include other protease recognition sequences suitable for generating α- or β-chains.

Where cellular expression is used to produce a fibrin chain precursor, the leader peptide can comprise any leader sequence known to enable specific proteolytic cleavage of the leader sequence from the fibrin chain precursor in the expression host (see below). The leader peptide additionally can have sequence encoding a "pre" function for targeting the precursor protein containing said peptide to an intracellular compartment or, preferably, to the outside. Where cellular expression is used to product a fibrin chain with an N-terminal extension, the extension polypeptide can be susceptible to partial or complete cleavage during the expression process. Additionally, the extension polypeptide can function to target the expressed protein.

Accordingly, the leader peptide of fibrin chain precursors or the N-terminal extensions can comprise the prepro sequence of any protein. In preferred embodiments, the prepro sequence is from a protein endogenous to the host cell or organism used to express the fibrin or fibrin-homologs or to a cell or organism evolutionarily closely related to the host cell or organism within which said prepro peptide is correctly recognized by the host. By the way of example and not limitation, listed below are proteins with prepro sequences that can be used in the construction of leader peptides of fibrin chain precursors. For expression in Saccharomyces the prepro (signal) sequence from the precursors of any of the following proteins can be used. Acid Phosphotase (PH05) (Perlman and Halvorsen, 1983, *J. Molec. Biol.*, 67:391–409; and α-Factor (Mfα) (Julius et al., 1984, *Cell*, 36:309–318; Brake et al., 1984, *Proc. Natl. Aced. Sci. USA*, 81:4642–4646; See also Kingsman et al., 1985, *Biotech. and Genet. Engineering Rev.*, 3:377–416). For expression in Aspergillus the prepro (signal) sequence from the precursors of any of the following proteins can be used. Chicken lysozyme signal sequence (Tsuchiya et al., 1992, *Appl. Microbiol. Biotechnol.*, 38:109–114); and glucoamylase (glnA) signal sequence (Jeenes et al., 1993, *FEMS Microbiol Lett.*, 107:267–272; Ward et al., 1990, *Biotechnol.*, 8:435–440).

Further, where the cleavage recognition site of a prepro peptide is known, the peptide sequence of the cleavage recognition site can be used to form the carboxy-terminal of the leader peptide. Examples of specific cleavage recognition sites that have been used to construct cleavable leader peptides include the thrombin cleavage recognition site (J. Y. Chang, 1985, *Eur. J. Biochem.*, 151–217–224), factor Xa cleavage recognition cleavage site (Nagai and Thorgensen, 1984, *Nature*, 309:810–812), and KEX2 cleavage site (Julius et al., ibid). See Smith and Johnson, 1988, *Gene*, 67:31–40, for examples of the use of thrombin and factor Xa cleavage recognition sites in forming cleavable leader peptides, and Kingsman et al., ibid for examples of the use of the KEX2 site. Preferred recognition sites are for proteases that are not derived from animals that are carriers or reservoirs for human pathogens, particularly viral pathogens.

Further, the leader peptide or N-terminal extension can additionally comprise sequences with properties that facilitate the purification of the fibrin chain precursor. The desired property can be based on any unique physical, chemical or biological property of the leader peptide that enables a selective separation of proteins that contain said peptide from those that do not. An example of such a "purification sequence" is a carboxyl-terminal portion of glutathione S-transferase (GST), which has a high affinity for glutathione. A fusion protein with a leader peptide comprising the GST purification sequence can be conveniently purified from cell extracts using glutathione-affinity columns. For a discussion of the use of GST purification sequence in the affinity purification of fusion proteins, see Smith and Johnson, ibid. Other purification sequences that can be used to form leader peptide useful in fusion protein purification include those to which there are readily available antibodies, e.g., β-galactosidase. Additional examples of peptides that can be used to facilitate fusion protein purification include transcription factors (Gabrielson and Huet 1993 *Methods in Enzymology* 218:508–525), phosphotyrosine-containing proteins and peptides (Frackelton et al., 1991, *Methods in Enzymology*, 201:79–92), and serine kinases (J. R. Woodgett, 1991, *Methods in Enzymology*, 200:169–178).

The leader peptide or N-terminal extension can be derived from a protein or polypeptide that has one or more of the aforementioned properties in the expression host. Alternatively, the leader peptide or N-terminal extension can be a composite of several different peptide sequences, each capable of conferring one or more of the aforementioned functions to the fibrin chain precursor in the expression host. In a composite leader peptide, the constituent sequences can be arranged in any order that preserves the full function of each sequence. Preferably, the sequence containing the protease cleavage recognition site forms the C-terminal of the composite leader peptide.

Fibrin chain precursors, fibrin chains, fibrinogen chains, fibrin, fibrin-homologs and fibrinogen-analogs can be produced by chemical synthesis, genetic engineering of cells or a combination thereof. In particular, fibrin chain precursors, extended fibrin chains, fibrin chains and fibrinogen chains can be chemically synthesized using procedures known in the art, such as commercially available peptide synthesizers and the like. Such standard techniques of polypeptide synthesis can be found described in such publications as Merrifield, 1963, *J. Chem. Soc.*, 85:2149–2154 and Hunkapillar et al., 1984, *Nature* (London), 310: 105–111).

In preferred embodiments, fibrin chain precursors, extended fibrin chains, fibrin chains and fibrinogen chains are produced by genetic engineering of cells and organisms (see below).

Fibrin monomers, fibrin-homologs and fibrinogen-analogs can be produced by in vitro processing of fibrin chain precursors (if necessary), and in vitro assembling of their constituent chains (i.e., fibrin chains and/or fibrinogen chains) into functional fibrin and fibrin-homologs (see Section 7.). Fibrin, fibrin-homologs and fibrinogen-analogs can also be produced by in vitro assembling of fibrin chains produced by genetic-engineering of cells and organisms. Further, fibrin monomers, fibrin-homologs and fibrinogen-analogs can also be produced completely in vivo, using genetic-engineered cells and organisms (see below). That is, genetic-engineered cells and organisms can be used to express and process the fibrin precursor chains and to assemble the resulting fibrin chains into fibrin monomers, fibrin-homologs and fibrinogen-analogs.

2. NUCLEOTIDE SEQUENCES ENCODING FIBRIN CHAIN PRECURSORS, FIBRIN CHAINS AND FIBRINOGEN CHAINS

The invention provides for nucleotide sequences which can be used to produce expression constructs useful in recombinant production of fibrinogen chains, fibrin chains, fibrin chain precursors, fibrin monomers, fibrin-homologs and fibrinogen-analogs. The properties of the nucleotide sequences provided herein are as varied as are the genetic structures of the various host cells and organisms that can be used to produce the fibrinogen chains, fibrin chains, fibrin chain precursors, fibrin monomers, fibrin-homologs and fibrinogen-analogs of the invention. The preferred embodiments will describe a number of features which an artisan will recognize as not being absolutely essential, but clearly advantageous. These include methods of isolation, synthesis or construction of iucleotide sequences and gene constructs, the manipulations of the sequences and constructs to be introduced into host cells and organisms, certain features of the sequences and constructs, and certain features of the vectors associated with the sequences and constructs.

Fibrinogen chains, fibrin chains, fibrin monomers, fibrin-homologs and fibrinogen-analogs can be produced by expressing, in a host cell or organism, the appropriate combination of expression constructs encoding fibrinogen chains, fibrin chains and fibrin chain precursors. See section 1 for the various combinations of polypeptide chains that form fibrin I monomers, fibrin II monomer, des BB fibrin monomer, fibrin I-homolog, fibrin II-homolog and des BB fibrin-homolog. Because α-chain and β-chain do not have a N-terminal methionine, their production by gene expression requires the use of constructs encoding α-chain precursors and β-chain precursors with leader peptides that can be cleaved off either in vitro or in vivo and thereby yielding the correct N-terminal sequence.

Nucleotide sequences encoding fibrinogen chains, fibrin chains, fibrin chain precursors and fibrin chains with N-terminal extensions can be constructed using any known method. The construction can use a single method or a combination of methods. The desired nucleotide sequences can be synthesized based on known or deduced amino acid sequences of the fibrin chains, fibrinogen chains and, in the instance of precursor chains, the combined sequences of the fibrin chain and the leader peptide. That is, the amino acid sequence is reverse-translated, from the genetic code, from the desired polypeptide sequence into one or more nucleotide sequences. See above for references containing amino acid sequences of fibrin chains and fibrinogen chains and leader peptides that can be used in such reverse-translations. In preferred embodiments, the codons usage of the reverse-translated coding sequence is in accordance with the preferred codon usage of the host cell or organism used to express the encoded polypeptide.

The synthesis of the desired nucleotide sequences can be achieved by standard chemical methods known in the art (e.g., see Hunkapillar et al., 1984, *Nature*, 310:105–111). Alternatively, the nucleotide sequence can be synthesized using polymerase chain reaction (PCR) amplification used in conjunction with chemically synthesized oligonucleotide primer fragments. For a review of PCR techniques, see for example, Gelfind, 1989, *PCR Technology. Principles and Applications for DNA Amplification*, Ed., H. A. Erlich, Stockton Press, N.Y.; *Current Protocols in Molecular Biology*, 1988, Vol. 2, Ch. 15, Eds. Ausubel et al., John Wiley & Sons; and Horton et al., 1989, *Gene*, 77:61–68.

Nucleotide sequences encoding fibrin chains, fibrinogen chains, fibrin chain precursors and fibrin chains with N-terminal extensions can also be constructed using recombinant DNA methodologies well known in the art. See, e.g., the techniques described in Sambrook et al., 1989, *Molecular Cloning: A Laboratory Manual*, 2nd. ed., Cold Spring Harbor Laboratory, Cold Spring Harbor, N.Y. Recombinant DNA methodologies can also be used to maintain, manipulate and/or recombine nucleotide sequences produced by other methods, e.g., chemical synthesis and PCR.

The construction of the desired nucleotide sequences using recombinant DNA methodology can be achieved by manipulating available cloned sequences of fibrinogen chains, fibrin chains and leader peptides. Such cloned sequences can be used directly in the construction, for example, by restriction digestion and ligation (see below).

Alternatively, the cloned sequences can also be used to construct nucleotide probes and the probes used to isolate genomic or cDNA clones encoding the desired chain or leader peptide from the appropriate genomic or cDNA libraries using standard methods. Such methods include, for example, the method set forth in Benton and Davis, 1977, *Science*, 196:180, for bacteriophage libraries, and Grunstein and Hogness, 1975, *Proc. Natl. Acad. Sci. U.S.A.*, 72:3961–3965, for plasmid libraries. Moreover, the nucleotide sequences can also be used to construct PCR oligonucleotide primers that can be used to amplify sequences encoding the desired chain, leader peptide or N-terminal extension from the appropriate genomic or cDNA library or genomic DNA. PCR can be carried out, e.g., by use of a Perkin-Elmer Cetus thermal cycler and Taq polymerase (Gene Amps). The nucleic acid being amplified can include mRNA or cDNA or genomic DNA. One can choose to synthesize several different degenerate primers for use in the PCR reactions. It is also possible to vary the stringency of hybridization conditions used in priming the PCR reactions, to allow for greater or lesser degrees of nucleotide sequence similarity between the unknown nucleotide sequence encoding fibrin chain, fibrinogen chain or leader peptide-containing protein and the nucleic acid homolog being isolated. After successful amplification of a segment of a desired coding sequence, that segment can be molecularly cloned and sequenced, and utilized as a probe to isolate a complete cDNA or genomic clone. It can also be used to design PCR primers for use in 5' RACE procedures that can be used to amplify sequence that is found, in the starting nucleic acid, adjacent to the originally amplified segment. For 5' RACE methods, see Frohman, "Rapid Amplification of cDNA for Generation of Full-Length cDNA," *Methods in Enzymology*, 218:340–356, 1993.

Any human cell (or cell derived from another fibrin-producing organism) potentially can serve as the nucleic acid source for the molecular cloning of sequences encoding fibrin chains and fibrinogen chains. Any cell or organism potentially can serve as the nucleic acid source for the cloning of sequences encoding the proteins that can serve as sources of components of leader peptides. The preferred source of "leader peptide components" is the host cell or organism used to express the fibrin chain, fibrin chain precursor or fibrin-homolog. The DNA can be obtained by standard procedures known in the art from cloned DNA (e.g., a DNA "library"), by cDNA cloning, or by the cloning of genomic DNA, or fragments thereof, purified from the desired cell. (See, for example, Sambrook et al., 1989, *Molecular Cloning, A Laboratory Manual*, 2d Ed., Cold Spring Harbor Laboratory Press, Cold Spring Harbor, N.Y.; Glover, D. M. (ed.), 1985, *DNA Cloning: A Practical Approach*, MRL Press, Ltd., Oxford, U.K. Vol. I, II). Clones derived from genomic DNA can contain regulatory and intron DNA regions in addition to coding regions; clones derived from cDNA will lack introns and will contain only exon sequences. Whatever the source, the coding sequence should be molecularly cloned into a suitable vector for propagation of the sequence.

In the molecular cloning of coding sequence from genomic DNA, DNA fragments are generated, some of which will encode the desired sequence. The DNA can be cleaved at specific sites using various restriction enzymes. Alternatively, one can use DNase in the presence of manganese to fragment the DNA, or the DNA can be physically sheared, as for example, by sonication. The linear DNA fragments can then be separated according to size by standard techniques, including but not limited to, agarose and polyacrylamide gel electrophoresis and column chromatography.

Once the DNA fragments are generated, identification of the specific DNA fragment containing the desired coding sequence can be accomplished in a number of ways. For example, if an amount of a portion of a fibrin chain gene or its specific RNA is available and can be purified, or synthesized, and labeled, the generated DNA fragments can be screened by nucleic acid hybridization to the labeled probe (Benton and Davis, 1977, *Science*, 196:180; Grunstein and Hogness, 1975, *Proc. Natl. Acad. Sci. U.S.A.*, 72:3961). Those DNA fragments with substantial homology to the probe will hybridize. It is also possible to identify the appropriate fragment by restriction enzyme digestion(s) and comparison of fragment sizes with those expected according to a known restriction map, either available or deduced from a known nucleotide sequence. Further selection can be carried out on the basis of the properties of the gene. Alternatively, the presence of the gene can be detected by assays based on the physical, chemical, or immunological properties of its expressed product. For example, cDNA clones, or DNA clones which hybrid-select the proper mRNAs, can be selected which produce a protein that, for instance, has similar or identical electrophoretic migration, isoelectric focusing behavior, proteolytic digestion maps, binding activity, or antigenic properties as known for a fibrin chain, fibrinogen chain or leader peptide-containing protein. By use of an antibody to the desired protein, the protein can be identified by binding of labeled antibody to the putative fibrin chain, fibrinogen chain or leader peptide-containing protein synthesizing clones, in an ELISA (enzyme-linked immunosorbent assay-type procedure.

Sequences encoding a fibrin chain, fibrinogen chain or leader peptide-containing protein can also be identified by mRNA selection by nucleic acid hybridization followed by in vitro translation. In this procedure, fragments are used to isolate complementary mRNAs by hybridization. Immunoprecipitation analysis of the in vitro translation products of the isolated products of the isolated mRNAs identified the mRNA and, therefore, the complementary DNA fragments that contain the desired sequences. In addition, specific mRNAs can be selected by adsorption of polysomes isolated from cells to immobilized antibodies specifically directed against a fibrin chain, fibrinogen chain or leader peptide-containing protein. A radiolabelled cDNA encoding fibrin chain, fibrinogen chain or leader peptide-containing protein can be synthesized using the selected mRNA (from the adsorbed polysomes) as a template. The radiolabelled mRNA or cDNA can then be used as a probe to identify the fragments encoding fibrin chain, fibrinogen chain or leader peptide-containing protein from among other genomic DNA fragments.

The identified and isolated coding sequence can then be inserted into an appropriate cloning vector. A large number of vector-host systems known in the art can be used. Possible vectors include, but are not limited to, plasmids, cosmids, or modified viruses or bacteriophages, but the vector system must be compatible with the host cell used. Such vectors include, but are not limited to, bacteriophages such as lambda and T4 phage derivatives, or plasmids such as pBR322 or pUC plasmid derivatives. The insertion into a cloning vector can, for example, be accomplished by ligating the DNA fragment into a cloning vector which has complementary cohesive termini. However, if the complementary restriction sites used to fragment the DNA are not present in the cloning vector, the ends of the DNA molecules can be enzymatically modified for instance, to allow for blunt-end ligation. Alternatively, any site desired can be produced by ligating nucleotide sequences (linkers) onto the DNA termini; these ligated linkers can comprise specific chemically synthesized oligonucleotides encoding restriction endonuclease recognition sequences. In an alternative method, the cleaved vector and sequence to be cloned can be modified by homopolymeric tailing. Recombinant molecules can be introduced into host cells via transformation, transfection, infection, electroporation, etc., so that many copies of the gene sequence are generated.

In an alternative method, the desired sequence can be dentified and isolated after insertion into a suitable cloning vector in a "shot gun" approach. Enrichment for the desired coding sequence, for example, by size fractionation, can be done before insertion into the cloning vector.

In specific embodiments, transformation of host cells with recombinant DNA molecules that incorporate the isolated fibrin chain, fibrinogen chain, leader peptide or N-terminal extension coding sequence, or synthetic DNA sequence enables generation of multiple copies of the gene. Thus, the gene can be obtained in large quantities by growing transformants, isolating the recombinant DNA molecules from the transformants and, when necessary, retrieving the inserted gene from the isolated recombinant DNA.

Cloned and synthesized nucleotide sequences encoding the fibrin chains fibrinogen chains and leader peptide-containing proteins can be further manipulated and used to construct sequences encoding the desired precursor chains using standard recombinant DNA methodologies. For example, where the desired leader peptide or N-terminal extension comprises peptide sequences from several different proteins (see above), the nucleotide sequences encoding each peptide can be spliced together into a continuous coding sequence and the composite coding sequence in turn spliced to the 5' end of a fibrin chain coding sequence. Such splicing can utilize any strategy known in the art, including the use of restriction endonuclease sites present on the respective coding sequences, artificial restriction sites introduced by in vitro mutagenesis or PCR amplification or restriction endonuclease sites on linkers ligated to the ends of cloned fragments. Similarly, since sequences derived from genomic DNA and cDNA can contain regulatory, leader RNA, intron and/or trailer RNA sequences that are not desirable in a fibrin chain precursor or fibrinogen chain construct, such extraneous sequences can be removed by any known recombinant DNA methodology including those discussed above.

3. NUCLEOTIDE SEQUENCES ENCODING VARIANT γ-CHAINS

The production and use of variant γ-chains (vγ-chains) are also envisioned and within the scope of the present invention. As discussed in Section 1, vγ-chain which result in the loss of fibrin D-domain function include but are not limited to any variant containing a mutation that disrupts the N-terminal distal intramolecular disulfide bond of the γ-chain. Particularly desireable mutations include missense mutations of Cys352 and/or Cys365 residue in the human γ-chain or the equivalent Cys in other γ-chains, or in-frame deletions removing the same residues. For example, useful missense mutations include those that result in an alanine or valine residue at one or both cystine sites. Additional useful mutations include but are not limited to any that alter the secondary and/or tertiary conformation of the vγ-chain at or near the Cys352 or Cys365 sites. These structural alterations can be such that the Cys residues cannot form an intrachain disulfide bond when the vγ-chain is incorporated into a fibrin or fibrinogen molecule.

The vγ-chains can be produced by various methods known in the art. The manipulations which result in their production can occur at the gene or protein level. The γ-chains can be altered at the gene level by site-specific mutagenesis using procedures known in the art. One approach that can be taken involves the use of synthetic oligonucleotides to construct variant γ-chains with base substitutions. In one embodiment, an oligonucleotide containing the desired mutation is synthesized and annealed to the single-stranded form of the wild-type γ-chain sequence (Zoller and Smith, 1984, *DNA*, 3:479–488). The resulting short heteroduplex can serve as primer for second strand synthesis by DNA polymerase. At the 5' end, a single-stranded nick is formed which is closed by DNA ligase. In another embodiment, two complementary oligonucleotides are synthesized, each containing the mutant sequence. The duplex that forms after annealing these complementary oligonucleotides, can be joined to a larger DNA molecule by DNA ligase provided that the ends of both molecules have complementary single-stranded "sticky" ends. Another approach that can be taken involves introducing a small single-stranded gap in the DNA molecule followed by mis-repair DNA synthesis i.e., the misincorporation of a non-complementary nucleotide in the gap (Botstein and Shortle, 1985, *Science*, 229:1193). The incorporation of a thiol nucleotide into the gap can minimize the excision of the non-complementary nucleotide. Alternatively, a variant γ-chain coding sequence can be prepared by chemically synthesizing the DNA using procedures known in the art (see, for example, Froehler, 1986, *Nucl. Acids Res.*, 14: 5399–5407 and Caruthers et al., 1982, *Genetic Engineering*, J. K. Setlow and A. Hollaender eds., Plenum Press, New York, vol. 4, pp. 1–17). In a preferred embodiment, fragments encoding segments of the variant γ-chain are chemically synthesized and these fragments are subsequently ligated together. The resulting variant γ-chain coding strands can be amplified using procedures known in the art, for instance PCR technology, and subsequently inserted into a cloning vector as described in Section 2. In a specific embodiment, site-specific mutants can be created by introducing mismatches into the oligonucleotides used to prime the PCR amplification (Jones and Howard, 1990, *Biotechniques*, 8:178–180).

Numerous ways of creating deletion mutants are well known in the art. See, for example, Sambrook et al., *Molecular Cloning: A Laboratory Manual*, 2nd ed., Cold Spring Harbor Press, 1989. These include, without limitation, methods making use of fortuitous restriction sites, exo-nuclease digestion strategies and amplifying partial-length sequences using PCR methods.

4. EXPRESSION OF FIBRIN CHAINS, FIBRIN CHAINS WITH N-TERMINAL EXTENSIONS AND FIBRINOGEN CHAINS

A nucleotide sequence coding for a fibrin chain, fibrin chain precursor, fibrin chain with an N-terminal extension or fibrinogen chain of the invention can be inserted into an appropriate expression vector, i.e. a vector which contains the necessary elements for the transcription and translation of the inserted protein-coding sequence. A variety of host-vector systems can be utilized to express the protein-coding sequence. These include but are not limited to mammalian cell systems infected with virus (e.g. vaccinia virus, adenovirus, retrovirus, etc.); insect cell systems infected with virus (e.g., baculovirus); plants or plant cells transformed with DNA or T-DNA vectors or transfected with viruses; microorganisms such as yeast or fungi containing yeast or fungal vectors, or bacteria transformed with bacteriophage, DNA, plasmid DNA or cosmid DNA.

The expression elements of vectors vary in their strengths and specificities. Depending on the host-vector system utilized, any one of a number of suitable transcription and translation elements can be used. Specific embodiments of the invention include the expression of each and every constituent chain of the fibrin and fibrin-homolog on the invention. Additional embodiments of the invention include simultaneous expression of particular combinations of fibrin chain, fibrin chain precursors, extended fibrin chains and fibrinogen chains that would enable production of complete and functional fibrin, fibrin-homologs or fibrinogen-analogs.

Any of the methods described herein for the insertion of DNA fragments into a vector can be used to construct expression vectors containing a chimeric gene consisting of appropriate transcriptional/translational control signals and the protein coding sequences. These methods can include in vitro recombinant DNA and synthetic techniques and in vivo recombination techniques (genetic recombination). Expression of a nucleotide sequence encoding a fibrin chain, fibrin chain precursor, fibrin chain with an N-terminal extension or fibrinogen chain can be regulated by a second nucleotide sequence so that the fibrin chain, fibrin chain precursor and fibrinogen chain is expressed in a host transformed with the recombinant DNA molecule. For example, expression of the desired protein can be controlled by any promoter/enhancer element known in the art. Promoters which can be used to control expression of the desired fibrin and fibrinogen chains include, but are not limited to, the SV40 early promoter region (Bernoist and Chambon, 1981, *Nature*, 290:304–310), the promoter contained in the 3' long terminal repeat of Rous sarcoma virus (Yamamoto, et al., 1980, *Cell*, 22:787–797), the herpes thymidine kinase promoter (Wagner et al., 1981, *Proc. Natl. Acad. Sci. U.S.A.*, 78:1441–1445), the regulatory sequences of the metallothionein gene (Brinster et al., 1982, *Nature*, 296:39–42) prokaryotic expression vectors such as the β-lactamase promoter (Villa-Kamaroff, et al., 1978, *Proc. Natl Acad. Sci. U.S.A.*, 75:3727–3731), the tac promoter (DeBoer, et al., 1983, *Proc. Natl. Acad. Sci. U.S.A.*, 80:21–25), the trpE promoter; see also "Useful proteins from recombinant bacteria" in *Scientific American*, 1980, 242:74–94; plant expression vectors comprising the opine synthetase promoter regions (Herrera-Estrella et al., *Nature*, 303:209–213) or the cauliflower mosaic virus 35S RNA promoter (Gardner, et al., 1981, *Nucl. Acids Res.*, 9:2871), and the promoter of the photosynthetic enzyme ribulose biphosphate carboxylase (Herrera-Estrella et al., 1984, *Nature*, 310:115–120); promoter elements from the following animal transcriptional control regions, which exhibit tissue specificity and have been utilized in transgenic animals: elastase I gene control region which is active in pancreatic acinar cells (Swift et al., 1984, *Cell*, 38:639–646; Ornitz et al., 1986, *Cold Spring Harbor Symp. Quant. Biol.*, 50:399–409; MacDonald, 1987, *Hepatology*, 7:425–515); insulin gene control region which is active in pancreatic beta cells (Hanahan, 1985, *Nature*, 315:115–122), immunoglobulin gene control region which is active in lymphoid cells (Grosschedl et al., 1984, *Cell*, 38:647–658; Adames et al., 1985, *Nature*, 318:533–538; Alexander et al., 1987, *Mol. Cell. Biol.*, 7:1436–1444), mouse mammary tumor virus control region which is active in testicular, breast, lymphoid and mast cells (Leder et al., 1986, *Cell*, 45:4ss–4s5)/albumin gene control region which is active in liver (Pinkert et al., 1987, *Genes and Devel.*, 1:268–276), alpha-fetoprotein gene control region which is active in liver (Krumlauf et al., 1985, *Mol. Cell. Biol.*, 5:1639–1648; Hammer et al., 1987, *Science*, 235:53–58); alpha 1-antitrypsin gene control region which is active in the liver (Kelsey et al., 1987, *Genes and Devel.*, 1:1 61–171), beta-globin gene control region which is active in myeloid cells (Mogram et al., 1985, *Nature*, 315:338–340; Kollias et al., 1986, *Cell*, 46:89–94); myelin basic protein gene control region which is active in oligodendrocyte cells in the brain (Readhead et al., 1987, *Cell*, 48:703–712); myosin light chain-2 gene control region which is active in skeletal muscle (Sani, 1985, *Nature*, 314:283–286), and gonadotropic releasing hormone gene control region which is active in the hypothalamus (Mason et al., 1986, *Science*, 234:1372–1378).

In preferred embodiments, the host system is a fungus, such as a yeast or filamentous fungus. Such systems for heterologous protein expression are highly advanced. Useful *Saccharomyces cerevisiae* expression vectors (and promoters) and hosts include any of those described by Kingsman et al., 1985, *Biotech. and Genet. Engineering Rev.*, 3:377–416; or S. C. Emr, 1990, *Meth. Enzymology*, 185:231. Useful non-Saccharomyces yeast expression vectors and hosts include any of those described by Reiser et al., 1990, *Adv. Biochem. Engineering Biotechn.*, 43: 75–102. Aspergillus vectors and hosts are also preferred expression systems for the present invention. Useful Aspergillus vectors and hosts include, but are not limited to, those described by Chevalet et al., 1993, *J. Biotechn.*, 27:239–246. (A. flavius expression vectors and host strains); Jeenes et al., 1993, *FEMS Microbiol. Lett.*, 107:267–272, Verdoes et al., 1993, *Transgenic Res.*, 2:8492, Archer et al., 1992, *Biotechn. Lett.*, 14:357–362, Roberts et al., 1992, *Biotechn. Lett.*, 14:897–902, Khanh et al., 1992, *Biotechn. Lett.*, 14:1047–1052, and Sharif et al., 1992, *Appl. Microbiol. Biotechn.*, 38:115–116 (*A. niger* expression vectors and hosts); Lachmund et al., 1993, *Current Microbiol.*, 26:47–51, and Ward et al., 1992, *Gene*, 122:219–223 (*A. nidulans* expression vectors and hosts), Ward et al., ibid., and Tsuchiya et al., 1992, *Appl. Microbiol Biotechnol.*, 38:109–114 (*A. oryzae* expression vectors and hosts). Particularly preferred hosts for in vivo production and secretion of fibrin and fibrin-homologs are host cells that can grow at pH 4.0 or lower. The low pH of the desired cultures may result from the acidic metabolisms of such hosts, i.e., production of acids, or artificial addition of acids to the culture media. Accordingly useful hosts include, but are not limited to, any of the Saccharomyces, Aspergillus, Streptococcus, Lactobacillus and Candida genera.

Expression vectors containing fibrin chain, fibrin chain precursor and fibrinogen chain inserts can be identified by three general approaches: (a) nucleic acid hybridization, (b) presence or absence of "marker" gene functions, and (c) expression of inserted sequences. In the first approach, the presence of a polypeptide coding sequence inserted in an expression vector can be detected by nucleic acid hybridization using probes comprising sequences that are homologous to the inserted sequence. In the second approach, the recombinant vector/host system can be identified and selected based upon the presence or absence of certain "marker" gene functions (e.g., thymidine kinase activity, resistance to antibiotics, transformation phenotype, occlusion body formation in baculovirus, and the like) caused by the insertion of heterologous sequence in the vector and the transformation of the host by the vector. For example, if a fibrin chain coding sequence is inserted within the marker gene sequence of the vector, recombinants containing the fibrin chain insert can be identified by the absence of the marker gene function. In the third approach, recombinant expression vectors can be identified by assaying the heterologous gene product expressed by the host cell. Such assays can be based, for example, on the physical or functional properties of the expression construct products in in vitro assay systems, e.g., fibrin polymer formation (see Hartwig and Danishefsky, 1991, *J. Biol. Chem.*, 266:6578–6585), immunoassays using antibodies directed to a fibrin chain, fibrin chain precursor or fibrinogen chain.

Once a particular recombinant DNA molecule is identified and isolated, several methods known in the art can be used to propagate it. Once a suitable host system and growth conditions are established, recombinant expression vectors can be propagated and prepared in quantity. As previously explained, the expression vectors which can be used include, but are not limited to, the following vectors or their derivatives: human or animal viruses such as vaccinia virus or adenovirus; insect viruses such as baculovirus; yeast vectors; bacteriophage vectors (e.g., lambda), and plasmid and cosmid DNA vectors, to name but a few.

In addition, a host cell strain can be chosen which modulates the expression of the inserted sequences, or modifies and processes the gene product in the specific fashion desired. Expression from certain promoters can be elevated in the presence of certain inducers; thus, expression of the genetically engineered fibrin chain, fibrin chain precursor and fibrinogen chain protein can be controlled. Furthermore, different host cells and organisms have characteristics and specific mechanisms for the translational and post-translational processing and modification (e.g., cleavage) of proteins. Appropriate cell lines or host systems can be chosen to ensure the desired modification and processing of the foreign protein expressed. Since different vector/host expression systems can effect processing reactions such as proteolytic cleavages to different extents, such differences afford opportunities to control the final protein product produced.

In specific embodiments, the host cell or organism is capable of recognizing both the targeting ("pre") and specific cleavage ("pro") signal sequences on the N-terminal extension or leader peptide. Such a host, when used to express a construct encoding a single fibrin chain precursor, would produce and secrete a mature (i.e., proteolytically processed) fibrin chain or a fibrin chain with a shortened N-terminal extension. The same host, when used to express constructs encoding the requisite fibrin chain precursors, fibrin chains and fibrinogen chains that comprise a fibrin or fibrin-homolog, would produce and secret a mature fibrin monomer, fibrin-homolog or fibrinogen-analog. In this regard, Aspergillus hosts are particularly preferred as they are highly versatile in correctly recognizing and processing targeting and cleavage signal from heterologous sources, ranging from bacteria to mammalian origin. See Gwynne et al., 1987, *Biotechnol.*, 5:369–376; Upshall et al., 1987, *Biotechnol.*, 5:1301–1304; Ward et al., 1992, *Gene*, 122:219–223; Tsuchiya et al., 1992, *Appl. Microbiol. Biotechnol.*, 38:109–114.

In other embodiments, the host cell or organism is capable of recognizing the targeting ("pre") but not a specific cleavage ("pro") signal sequences on the N-terminal extension or leader peptide. Such a host, when used to express a construct encoding a single fibrin chain precursor or fibrin chain with an N-terminal extension, secrets a fibrin chain precursor or fibrin chain with an N-terminal extension. The same host, when used to express constructs encoding the requisite fibrin chain precursors, N-terminally extended fibrin chains, fibrin chains and fibrinogen chains that comprise a fibrin monomer, fibrin-homolog, or fibrinogen-analog secretes a precursor of fibrin monomer, a precursor of fibrin-homolog or a fibrinogen-analog. The fibrin chain precursor, fibrin monomer precursor or fibrin-homolog precursor thus produced can be further processed in vitro (ile. cleaved with the appropriate processing protease) to produce the corresponding mature polypeptide or protein. For example, where the leader peptide of the fibrin chain, fibrin monomer or fibrin-homolog precursor contains a factor $X_a$ recognition site, the leader peptide(s) can be cleaved by in vitro digestion with factor Xa. See Smith and Johnson, ibid.

In further embodiments, the host cell or organism is incapable of recognizing a targeting ("pre") or a specific cleavage ("pro") signal sequence on the leader peptide of the fibrin chain precursor or fibrin chain with an N-terminal extension. Such a host, when used to express a construct encoding a fibrin chain precursor or fibrin chain with an N-terminal extension, would produce and sequester a fibrin chain precursor or an otherwise extended fibrin chain. The same host, when used to express constructs encoding the requisite fibrin chain precursors, N-terminally extended fibrin chains, fibrin chains and fibrinogen chains that comprise a fibrin monomer, fibrin-homolog or fibrinogen-analog, would produce and sequester a precursor of fibrin, a precursor of fibrin-homolog or a fibrinogen-analog. The fibrin chain, fibrin or fibrin-homolog precursors thus produced can be harvested from the host cell and further processed in vitro (i.e. cleaved with the appropriate processing protease) to produce the corresponding mature polypeptide or protein.

The invention also provides for engineering the host cell or organism, where appropriate, with the required secretory and/or processing functions that would allow for the secretion and/or processing of the fibrin chain precursors or the fibrin monomers and fibrin-homologs comprising such precursors. For example, where the leader peptide of a fibrin chain precursor comprises a factor $X_a$ or thrombin cleavage recognition site, the host cell or organism can be engineered with a expression construct encoding factor $X_a$ or thrombin so as to enable the proper cleavage of the leader peptide from a fibrin chain precursor or the precursor of fibrin or fibrin-homolog assembled from such fibrin chain precursors. Similarly, where the transport or membrane function for a particular targeting sequence has been identified, that function can be introduced into a secretory deficient host cell or organism by genetic engineering or, where possible, by traditional genetic manipulations in order to enable the desired targeting or secretion of leader peptide containing proteins, whether they be fibrin chain precursors or precursors of fibrin, fibrin-homologs or fibrinogen-analogs.

5. IDENTIFICATION AND PURIFICATION OF THE EXPRESSED GENE PRODUCTS

Once an expression construct for a particular coding sequence is identified, the expression of the desired gene product can be analyzed and the protein product purified. Analysis of the expressed product can be achieved by assays based on the physical or functional properties of the product, including sedimentation centrifugation; immunoassays such as western blots and ELISA using gene-product specific antibodies (see Section 6.); HPLC; gel electrophoresis; fibrin polymer formation (Hartwig and Danishefsky, ibid.); etc.

Fibrin chain precursor, fibrin chain, fibrin monomer, fibrin-homolog or fibrinogen-analog can be isolated and purified from contaminants by standard methods including chromatography (e.g., ion exchange, affinity, and sizing column chromatography), centrifugation, differential solubility, or by any other standard technique for the purification of proteins. See Murano et al., 1971, *FEBS Lett.*, 14:37–41 for a procedure that separates the individual fibrin chains using CM/cellulose chromatography. Where the leader peptide or N-terminal extension contains a "purification-facilitating" moiety or sequence, the fibrin chain precursor, N-terminally extended fibrin chain, fibrin precursor, fibrin-homolog precursor or fibrinogen-analog can be purified using the corresponding affinity method (e.g., a gluthionine column for proteins containing a GST-derived leader peptide, an antibody column or immunoprecipitation for proteins containing a leader peptide to which specific antibodies exist, etc.). Further, the individual fibrin chains, fibrin chain precursors or extended fibrin chains can be purified using immunoaffinity methods using monoclonal or polygonal antibodies specific for the individual fibrin chains (i.e., α-, β- γ- or vγ-chain) (See Section 6.).

Fibrin monomers, fibrin-homologs and fibrinogen-analogs and their precursors can also be purified based on their ability to spontaneous form "soluble" non-covalently bonded polymers. In specific embodiments, precursors of fibrin monomers, fibrin-homologs and fibrinogen-analogs (i.e., with leader peptide or N-terminal extension present on one or more of their constituent chains) can be in vitro processed with the appropriate "cleavage site specific" protease (e.g., factor Xa or thrombin). The in vitro or in vivo processed fibrin monomer and fibrin-homolog can be initially purified using any of the aforementioned, conventional biochemical procedures in buffers that prevent polymerization (for instance, buffers having pH$\geq$4.0). When fibrin monomers or self-polymerizable fibrinogen-analogs are produced, the fibrin monomers or fibrinogen-analogs are then allowed to polymerize by neutralizing the buffer and purified by filtration through any suitable filter that can separate the fibrin polymer from any soluble contaminates. Suitable filters include a sintered polypropylene 20 micron pore size filter from Porex, Inc., a teflon 20–70 micron pore size filter from Fluorotechniques, Inc. or a nylon 66 22–46 micron pore size filter from Costar, Inc. The functional properties of the fibrin chain, fibrin monomer, fibrin-homolog or fibrinogen-analog produced can be evaluated using any suitable assay, including, but not limited to, assembly into a fibrin, fibrin-homolog or fibrinogen-analog and fibrin polymer formation.

6. ANTIBODIES TO FIBRIN CHAINS

Substantially pure fibrin chain preparations produced by using any known methods can be used as immunogens to generate specific antibodies to each fibrin chain (i.e., α, β γ or vγchain) and to their precursors. Such antibodies can be polyclonal, monoclonal, chimeric, single chain, Fab fragments, or from a Fab expression library. Various procedures known in the art can be used for the production of polyclonal antibodies to a fibrin chains. In particular embodiments, rabbit polyclonal antibodies to each fibrin chain can be obtained. For the production of antibody, various host animals can be immunized by injection with a recombinantly produced fibrin chain, or a synthetic version, or fragment thereof. Useful hosts include, but are not limited to, rabbits, mice, rats, etc. Various adjuvants can be used to increase the immunological response, depending on the host species, and including but not limited to Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and corynebacterium parvum.

For preparation of monoclonal antibodies directed toward a fibrin chain or fibrin chain precursor, any technique which provides for the production of antibody molecules by continuous cell lines in culture can be used. For example, the hybridoma technique originally developed by Kohler and Milstein, 1975, *Nature*, 256:495–497), as well as the trioma technique, the human B-cell hybridoma technique (Kozbor et al., 1983, *Immunology Today*, 4:72), and the EBV-hybridoma technique to produce human monoclonal antibodies (Cole et al., 1985, in *Monoclonal Antibodies and Cancer Therapy*, Alan R. Liss, Inc., pp. 77–96).

Antibody fragments which contain the idiotype (binding domain) of the molecule can be generated by known techniques. For example, such fragments include but are not limited to: the F(ab')2 fragment which can be produced by pepsin digestion of the antibody molecule; the Fab fragments which can be generated by reducing the disulfide bridges of the F(ab')2 fragment, and the Fab fragments which can be generated by treating the antibody molecule with papain and a reducing agent.

In the production of antibodies, screening for the desired antibody can be accomplished by techniques known in the art, e.g. ELISA (enzyme-linked immunosorbent assay), western blot, immunodiffusion assays. For example, to select antibodies which recognize α-chain, one can assay generated hybridomas for a product which binds to an substantially pure α-chain, fibrin or fibrinogen preparation.

The foregoing antibodies have utility in immunoassays of fibrin chains, fibrin chain precursors, fibrin monomers, fibrin-homologs or fibrinogen-analogs as described in Section 5. The antibodies also have utility as a reagent for immunoaffinity purification of fibrin chains, fibrin chain precursors, fibrin or fibrin-homologs as described in Section 5.

7. IN VITRO ASSEMBLY OF FIBRIN, FIBRIN HOMOLOGS AND THEIR PRECURSORS

Another aspect of the invention provides for the in vitro assembly of fibrin monomer, fibrin-homologs and fibrinogen-analogs and their precursors from their constituent chains. Any procedure known in the art for the assembly of proteins from their constituent polypeptides can be used. The assembly procedure generally involves preparing an equimolar solution of the three constituent chains of a fibrin monomer, fibrin-homolog, fibrinogen-analog or their precursors (e.g., for fibrin I monomer: α-, Bβ-, and γ-chains; for fibrin I homolog: α-, Bβ-, and vγ-chains; for fibrin I precursor: γ-chain precursor, Bβ-, and α-chains; etc.) in the presence of a chaotropic agent (denaturant) and a reducing agent and gradually removing the denaturant and reducing agent by dialysis. Under the appropriate conditions such procedures will assemble the constituent chains into a functional fibrin, fibrin-homolog or, in the instance of fibrin or fibrin-homolog precursors, precursor proteins that can be subsequently processed to form a functional fibrin or fibrin-homolog. Other ratios of component chains can be used. In a preferred embodiment, the molar ratio of any heterologous pair of chain preparatory used in the assembly process is no more than about 1.5:1.

More particularly, the assembly procedure utilizes as the assembly reaction an approximately equimolar mixture of each constituent fibrin chain, from about 0.1 mg/ml to about 6.0 mg/ml per chain preparation, dissolved in Initial Assembly (IA) solution comprising a chaotropic agent and a reducing agent. In preferred embodiments, each of the three chain preparations (e.g., for assembling fibrin I: α-, Bβ- and γ-chain preparations) is dissolved in IA solution at about 2.0 to about 4.0 mg/ml. While chain preparations of any purity can be used in the assembly procedure, it is preferred that substantially pure chain preparations (>50% pure by weight) and more preferred that highly pure chain preparations (>80% pure by weight) be used.

The IA solution comprises a high concentration of one or more chaotropic agent (denaturant). Suitable chaotropic agents include urea, sodium bromide, guanidine hydrochloride, KCNS, potassium iodide and potassium bromide. While any denaturant can be used, the preferred denaturant is urea, at a concentration of about 0.5 M, preferably 2.5 M, or higher. The urea concentration is more preferably about 3.5 M or higher, still more preferably at least about 5.0 M or higher. Comparable protein unfolding concentrations of other denaturants can be substituted for urea. The IA solution additionally comprises one or more reducing agents, such as dithiothreitol (DTT), dithioerythreitol (DTE) or β-mercaptoethanol. The concentration of the reducing agent in the IA solution can range from about 0.05 mM to about 100 mM. In preferred embodiments, the reducing agent is DTT at a concentration from about 5 to about 10 mM. The IA solution additionally comprises a buffer such as Tris-HCl or Tris-acetate. The buffer concentration is preferably from about 10 to about 50 mM and its pH ranges from about 6.5 to about 8.5. In preferred embodiments, the buffer is Tris-HCl at about 10 mM and about pH 7. The IA solution further comprises one or more divalent cation chelators. Nonlimiting examples of chelators include citric acid, saccharic acid, ethylenediaminetetraacetic acid (EDTA), nitrilotriacetic acid (NTA), hydroxyethylenediamine-triacetic acid (HEEDTA), ethylenediaminedi-[o-hydroxyphenylacetic acid] (EDDHA), ethyleneglycolbis (2-aminoethylether) tetraacetic acid (EGTA), diethylenetriaminepentaacetic acid (DTPA), 1,2-diaminocyclohexanetetraacetic acid (DCTA), N,N-bishydroxyethylglycine, and N-hydroxyethyliminodiacetic acid (HIMDA) and salts thereof. The preferred chelator is EDTA or EGTA, and its concentration is from about 0.1 mM to about 5 mM.

The assembly of the fibrin monomer, fibrin-homolog, fibrinogen-analog and their precursors from their constituent chains in the IA solution proceeds by a removal of the denaturant and the reducing agent. Any method known in the art can used to effect the removal. The removal can be achieved through stepwise dialysis of 5 or more equal steps to a final buffered solution devoid of the denaturant and reducing agent (e.g., a 5 equal-step dialysis from a 5 M urea, 15 mM DTT IA solution would consists of dialyzing, sequentially, against solutions containing 4 M urea, 0 mM DTT; 3 M urea, 0 mM DTT; 2 M urea, 0 mM DTT; 1 M urea, 0 mM DTT; and 0 mM urea, 0 mM DTT. In some embodiments a continuous gradient dialysis system can be used.

The dialysis solutions used at each step of the assembly reaction are preferably identical in composition to the IA solution except for the absence of reducing agent and the reductions in the denaturant. In particular embodiments, the dialysis solutions used for reducing the denaturant concentration from about 1 M and lower can additionally comprise glutathione/oxidized-glutathione, or CuSO4 to facilitate disulfide bond formation within the assembled fibrin monomer or fibrin-homolog. Where applicable, the preferred concentrations of glutathione and oxidized-glutathione are about 1 to 3 mM and 0.3 to 0.5 mM, respectively, and the preferred concentration of CuSO4 is at about 80 mM.

The temperature of assembly reaction is preferably from about 4° C. to about 65° C. The preferred temperature for the reaction is from about 20° C. to about 50° C., more preferably about 25° C.

The rate of dialysis of the assembly reaction can be regulated using any known means. For example, the ratio of membrane surface to assembly reaction volume can be increased or decreased to increase or decrease the rate of solute exchange and hence the time needed to reach solute equilibrium. Each dialysis step of the assembly process preferably uses a dialysis rate that produces an equilibrium from about 15 minutes to about 180 minutes. A particularly preferred rate achieves solute equilibrium within about 60 minutes.

For fibrin monomer and self-polymerizing fibrinogen-analog, the assembled molecule will generally polymerize as dialysis proceeds. Preparations of assembled and polymerized fibrin or fibrinogen-analog can be solubilized using any solution that results in release of monomers from the fibrin or fibrin-homolog polymer. Solubilization can be carried out by dialyzing the preparation or dissolving fibrin polymer clot collected from the assembly reaction with a suitable acid buffer solution. The acidic buffer has a pH of about 1 to about 5 and preferably at about 4. The preferred concentration of the acid buffer is from about 0.02 M to about 1 M and most preferably from about 0.1 M to about 0.3 M. Nonlimiting examples of suitable acid buffer include acetic acid, succinic acid, glucuronic acid, cysteic acid, crotonic acid, itaconic acid, glutamic acid, formic acid, aspartic acid, adipic acid and salts hereof and with succinic acid, aspartic acid, adipic acid and salts of acetic acid being preferred and most preferably sodium acetate.

The fibrin monomer, fibrin-homolog and fibrinogen-analog preparations can be further purified of any contaminates using any known physical, chemical or biochemical method.

8. USES FOR THE RECOMBINANT FIBRIN CHAINS, FIBRIN AND FIBRIN-HOMOLOGS

Fibrin chains, fibrin monomers, fibrin-homologs and fibrinogen-analogs of large quantity and high purity can be obtained using the methods of the present invention. Examples of fibrin chains which can be obtained include α-chain, β-chain, γ-chain and vγ-chain. Examples of fibrin which can be obtained include fibrin I, des BB fibrin and fibrin II. Examples of fibrin-homologs which can be obtained include fibrin I-homolog, des BB fibrin-homolog and fibrin II-homolog. An example of a fibrinogen-analog is a molecule made up of two α-chains with an N-terminal extension that differ from the A fibrinopeptide, two β-chains and two γ-chains. The fibrin chains, fibrin monomers, fibrin-homologs and fibrinogen-analogs will preferably be substantially free of cellular material and completely free of contagious viral agents that are sometimes found in human blood derived products. The fibrin monomer and fibrin-homologs can be used in preparation of fibrin-monomer sealants. See, for instance, the methods disclosed in Edwardson et al., European Patent Publication No. 0592242A1 (Apr. 13, 1994).

The invention also relates to a method of forming a fibrin polymer sealant by reacting a first fibrin-related protein that is incapable of self-polymerizing with a second fibrin-related protein the is incapable of self-polymerizing. An example of the first fibrin-related protein is fibrin-homolog (which contains two modified γ-chains). Examples of the second include fibrinogen and those fibrinogen-analogs that are incapable of self-polymerizing. These non-self-polymerizing fibrinogen-analogs will generally have N-terminal extensions on their α-chains and β-chains (for a total of four extensions). The two component fibrin-related protein compositions are preferably reacted at a molar ratio ranging from about 2:1 to about 1:2, more preferably from about 1.5:1 to about 1:1.5. Suitable buffer conditions are the same as those used for other fibrin-monomer sealants. See EP 0592 242 A1. The two compositions preferably contain no more than about 20% wt/wt, more preferably no more than about 10%, yet more preferably no more than about about 5% of a fibrin-related protein that self-polymerizes.

Moreover, the fibrin chains, fibrins and fibrin-homologs can be used to form bioactive fragments of fibrin that function in regulating angiogenesis, platelet aggregation, fibrin polymerization, cell proliferation, and the like.

The following examples are presented by way of illustration not by way of limitation.

9. EXAMPLES
9.1. CONSTRUCTION OF EXPRESSION CONSTRUCTS
9.1.1. α-CHAIN CONSTRUCT

Primers PCR1A and PCR2A (FIG. 5, SEQ ID NOS: 8 and 9, respectively) were used to amplify an approximately 560 base pair fragment from a human fibrinogen Aα-chain cDNA clone. This fragment was digested with Hind III and XbaI and cloned into a Hind III and XbaI cut Bluescript II KS+ Plasmid (Strategne). The sequence of this fragment, encoding a N-terminal portion of α-chain, was checked and the clone designated pBSalpha1.

pBSalpha1 was digested with KpnI and MluI and the synthetic leader sequence shown in FIG. 1 (SEQ ID NOS: 1 and 2) was inserted. The sequence of this clone was checked and the clone designated pBSalpha2.

An Aα-chain cDNA clone was digested with XbaI and NotI and the insert, encoding a C-terminal portion of α-chain, was purified. This fragment was inserted into a similarly digested pBSalpha2. The clone thus generated pBSalpha3, encodes a complete α-chain. The complete sequence of this construct was checked before sub-cloning into an expression vector. The construct was removed by digestion with KpnI/NotI was inserted into the expression vector pREP4 (Invitrogen).

9.1.2. β-CHAIN CONSTRUCT

Primers PCR1B and PCR2B (FIG. 5, SEQ ID NOS: 14 and 15, respectively) were used to amplify an approximately 750 base pair fragment from a human fibrinogen Bβ-chain cDNA clone. This fragment was digested with Hind III and BamHI and cloned into a Hind III and BamHI cut pBluescript II KS+ plasmid. The sequence of this fragment, encoding a N-terminal portion of β-chain, was checked and the clone designated pBSbeta1.

pBSbeta1 was digested with KpnI and Hind III and the synthetic leader sequence shown in FIG. 2 (SEQ ID NOS: 3 and 4) was inserted. The sequence of this clone was checked, and the clone designated pBSbeta2.

A Bβ-chain cDNA clone was digested with BamHI and NotI and the insert, encoding a C-terminal portion of β-chain, was purified. This fragment was inserted into a similarly digested pBSbeta2. The clone thus generated, pBSbeta3, encoded a completed β-chain precursor. The complete sequence of this construct was checked before sub-cloning into an expression vector. The construct was removed by digestion with KpnI and NotI and inserted into the expression vector pREP8 (Invitrogen).

9.1.3. γ-CHAIN CONSTRUCT

Primer PCR1G and PCR2G (FIG. 5, SEQ ID NOS: 22 and 23, respectively) were used to amplify an approximately 310 bp fragment from a human fibrinogen γ-chain cDNA clone. This fragment was digested with SphI and EcoRI and cloned into a SphI and EcoRI cut mp19 vector containing a γ-chain cDNA clone (the SphI/EcoRI digest of the vector removed the 3' portion of the cDNA clone, which sequence was replaced with the sphI/EcoRI fragment). The sequence of this clone was checked and designated mp19-gammal.

Double-strand RF-DNA was prepared from mp19-gammal and digested with AvrII and EcoRI. The synthetic 3' fragment shown in FIG. 3 was inserted. The sequence of the resultant clone was checked, and the clone designated mp19-gamma2. This clone contained a full-length gamma-fibrinogen (γ-chain) insert.

The insert was isolated as a SalI and NotI fragment from mp19-gamma2 ds RF-DNA and ligated into a KpnI and NotI cut pREP9 (Invitrogen) with the inclusion of the KpnI/SalI adaptor (SEQ ID NO: 28, as shown in FIG. 4) in the ligation reaction. The structure of the insert was verified with sequencing. This clone was designated gamma-pREP9.

9.1.4. γ-CHAIN MUTAGENESIS

Here, the CYS352 and CYS365 codons of γ-chain cDNA were substituted with ALA codons and cloned into pREP9.

A fragment of approximately 400 b.p. was isolated from gamma-pREP9 using SphI (position 1057 in insert) and BamHI (site present in the vector polylinker, 3' to NotI site) and was cloned into M13mp18. The sequence of this clone (mp18-gammal) was verified by sequencing.

A culture of dut-minus, ung-minus *E. coli* strain RZ1032 was infected with recombinant mp18-gammal and uracil-substituted single stranded mp18-gammal DNA was prepared. This was used as a template for site directed mutagenesis using primer MUTIG (6'-TTTGAAGGCAACGCTGCTGAACAGGA-3', SEQ ID NO: 29) and MUT2G (5'-ACAAGGCTCACGCTGGCCATCTCAATGG-3', SEQ ID NO: 30). Clones with both target CYS to ALA codon alterations were identified using a combination of 3' mismatch PCR, using primers PCRY (5'-GATCCATCCTGTTCAGCAGC-3', SEQ ID NO: 31) and PCRX (5'-GGTTGGTGGATGAACAAGGC-3', SEQ ID NO: 32) and routine sequencing. (See. FIG. 7).

The resultant clone (mp18-gamma2) was sequenced between the SphI and NotI sites. This SphI/NotI fragment was simultaneously ligated into a KpnI and NotI cut pREP9 along with a KpnI/SphI fragment from gamma-pREP9 encoding a N-terminal portion of the γ-chain. The resultant clone (gammaALA-pREP9) was purified on a CsCl gradient and sequenced across the 5' end and between the SphI site at position 1057 of the γ-chain sequence and the 3' end in order to validate the construct.

9.1.5. PREPARATION OF OLIGONUCLEOTIDES

Oligonucleotides (FIG. 5) used in these constructions were 5' phosphorylated, except for terminal oligos (A1, A4, B1, B6, G1, G2, SEQ ID NOS: 10, 13, 16, 21, 24 and 25). Phosphorylation was achieved during synthesis using a 5' phosphorylation reagent, or post-synthesis using T4 polynucleotide kinase.

Oligonucleotide pairs (A1/A2 (SEQ ID NOS: 10 and 11), A3/A4 (SEQ ID NOS: 12 and 13), etc.) were mixed at equimolar concentrations, heated to 95° C., and allowed to anneal by slow cooling to <30° C. Annealed pairs A1/A2 and A3/A4 or B1/B2, B3/B4 and B5/B6 (SEQ ID NOS: 10–13 and 16–21) were mixed at equimolar concentrations and ligated at room temperature. These ligations allowed the synthetic preparation of polynucleotides encoding complete leader sequences.

By leaving the terminal oligonucleotides un-phosphorylated, concatenation of the fully assembled fragment was prevented. This full length product was purified by gel electrophoresis before insertion into the relevant vector.

9.1.6. *ASPERGILLUS NIGER* EXPRESSION VECTORS

Fibrin alpha cDNA was cloned in two steps using XbaI-minus derivative of the GAM-fusion vector pIGF (FIG. 6). Initially, the XbaI site of pIGF was removed by cutting the plasmid with XbaI and HpaI and inserting by ligation a synthetic XbaI/HpaI linker:

5'-CTAGCGCCGGGGTT-3'
    GCGGCCCCAA (SEQ ID NO: 33 for the (+) strand and SEQ ID NO: 34 for the complementary strand) which resulted in the loss of the XbaI site but retention of the HpaI site, without altering the reading frame and without introducing stop codons.

Approximately the first 570 base pairs (bp) of the mature alpha-fibrin cDNA were amplified by PCR using oligo primers to remove the signal sequence from alpha-pREP4 and to introduce a HpaI site and KEX2 endoprotease processing site just upstream and in-frame with amino-terminus (sequence introduced: AAT TTC GTT AAC AAG CGC GGC CCA CGC GTT GTG GAA (SEQ ID NO: 35), which encodes a HpaI site, followed by the peptide LysArg-GlyProArgValValGlu (SEQ ID NO: 36), containing a KEX2 processing site) and a HpaI site just downstream of the XbaI site at 634 bp. This PCR fragment was cut with HpaI, gel-purified and cloned into the HpaI site of the XbaI-minus pIGF derivative. Clones with the insert in the correct orientation were sequenced to check for the presence of the GAM (G498)-fusion, the KEX2 site and the alpha-fibrin sequence up to the XbaI/HpaI sites. This clone is designated pIGF-alpha5'.

An XbaI site has been introduced at the NotI site in alpha-pREP4 using a synthetic NotI-XbaI-NotI linker. The resulting 1310 bp XbaI fragment containing the remainder of the alpha-fibrin cDNA was gel-purified and cloned into the correct pIGF-alpha5' clone, cut with XbaI.

Fibrin beta cDNA was also cloned using a two-step procedure but using a StuI-minus derivative of pIGF. pIGF has been cut with StuI, a blunt-end cutter (AGGCCT), and the single site at the extreme 5' end of the glaA 5'-flanking region will be destroyed using terminal transferase and a mixture of dideoxy ATP/TTP.

9.2. IN VITRO ASSEMBLY OF FIBRINOGEN AND FIBRIN

Ten mg of fibrinogen was denatured and dissociated per ml of 5 M urea, 5 mM DTT, 10 mM Tris-HCl, 1 mM EDTA, pH 7.0. The urea and the DTT was removed from the above "assembly" reaction by stepwise dialysis, each step for 1 hour at room temperature, in 10 mM Tris-HCL, 1 mM EDTA, pH 7.4 dialysis buffers containing 4 M, 3 M, 2 M, 1 M and 0 M urea. The final preparation polymerized when thrombin was added at 10 U/ml, both in the presence or absence of 5 mM CaCl2. The clot formation indicated the successful assembly of fibrinogen, which was converted by the thrombin to fibrin, which polymerized.

Fibrin assembly was performed as follows. Ten mg of fibrinogen was digested with 10 U/ml thrombin. The reaction containing fibrin was then brought to a final concentration of 10 mg/ml of fibrin in 5 M urea, 5 mM DTT, 10 mM Tris-HCl, 1 mM EDTA, pH 7.4. The denatured and dissociated fibrin was assembled following the sequential dialysis procedure described above, i.e., against dialysis buffers containing 4 M, 3 M, 2 M, 1 M and 0 M urea. At the 1 M urea stage, samples removed from the dialysis tube contained recognizable clot, indicating successful assembly of fibrin. Samples removed from the dialysis tube 20 minutes after transferred to the 0 M urea buffer contained a stronger (whiter) clot, indicating that the assembly reaction at the 1 M urea stage was incomplete.

9.3. DELETIONAL ANALYSIS OF THE γ-CHAIN

One deletion mutant is created by digesting gamma-pREP9 with SphI and inserting a double stranded SphI adapter designed to encode a stop codon after Met 336. Other deletion mutants are constructed using essentially the methodology described in Example 9.1.2 with three changes. First, the 3' PCR primer is designed based any of the between that encoding Met 336 and that encoding the C-terminus. Second, the 3' fragment is not added to the amplified sequence. Third, the 5' end of the primer includes the appropriate restriction site sequences for cloning into the mp19 and pREP9 vectors.

9.4. HETEROLOGOUS FIBRIN SEALANTS MADE USING CYS-MODIFIED FIBRIN AND FIBRINOGEN

Fibrin II-homolog containing variant γ-chain (Cys 352-Ala 352, Cys 365-Ala 365) at 100 μg/ml dissolved in 0.15 M NaCl, 0.05 M Tris, pH 7.0, is mixed with equal volumes of fibrinogen containing variable concentrations (10 μg/ml–1000 μg/ml, in the same buffer) and incubated at 37° C. Polymerization is assessed by visual inspection and an heterologous fibrin polymer is evident in solutions containing molar ratios of fibrinogen:fibrin II-homolog of 1:0.5 to 1:2.0.

A native, human fibrinogen was modified using the procedure outlined in Procyk et al., *Biochemistry* 31: 2273–2278, 1992 and Procyk et al., European Patent Publication No. 472 205 A1 (see Examples 1 and 2) such that a number of the Cys residues, including Cys 352 and 365, were reduced under mild reducing conditions and alkylated. The alkylated fibrinogen was activated by treatment with thrombin to remove the majority of the fibrinopeptides and create a fibrin monomer as described by Procyk et al. Id. The alkylated fibrin monomer lacks the ability to self-polymerize and is therefore a fibrin-homolog. The alkylated fibrin-homolog was dissolved at 100 μg/ml in 0.15 M NaCl, 0.05 M Tris, pH 7.0, mixed with an equal volume of a fibrinogen solution (10 μg/ml–1000 μg/ml) in the same buffer, and incubated at 37° C. Polymerization was assessed by visual inspection and an heterologous fibrin polymer was evident in solutions containing molar ratios of fibrinogen:fibrin-homolog of 1:0.5 to 1:2.0.

The invention described and claimed herein is not to be limited in scope by the specific embodiments herein disclosed, since these embodiments are intended as illustrations of several aspects of the invention. Any equivalent embodiments are intended to be within the scope of this invention. Indeed various modifications of the invention in addition to those shown and described herein will become apparent to those skilled in the art from the foregoing description. Such modifications are also intended to fall within the scope of the appended claims.

What is claimed is:

1. A fibrin sealant comprising human fibrin-homolog, wherein said human fibrin-homolog comprises recombinant variant fibrin gamma-human comprising:
   recombinant variant fibrin gamma-chain that differs from naturally occurring human fibrin gamma-chain by one or more mutations or deletions in a C-terminal region following a coiled-coil forming region such that when incorporated into fibrin-homolog, the homolog lacks the ability to substantially self-polymerize but has the ability to form non-covalent bonds and thereby polymerize with fibrinogen.

2. The fibrin sealant of claim 1, wherein the mutations or deletions occur in the sequence between about the potition of the first of the two conserved Cys residues found in the C-terminal portion of gamma-chains and the C-terminal.

3. The fibrin sealant of claim 1, wherein the mutations or deletions are in the sequence between amino acid 166 and the C-terminal of the gamma-chain.

4. The fibrin sealant of claim 3, wherein the variant fibrin gamma-chain has a mutation or deletion of a Cys residue selected from the group consisting of Cys residues 352 and 365 of the naturally occurring human fibrin gamma-chain.

5. A fibrin-related mix polymer composition comprising:
   (1) a fibrin-homolog composition comprising a modified fibrin gamma-chain that differs from naturally occurring human fibrin gamma-chain by one or more mutations deletions or modifications in a C-terminal region following a coiled-coil forming region such that, when incorporated into fibrin-homolog, the homolog lacks the ability to substantially self-polymerize but has the ability to form non-covalent bonds with fibrinogen; and
   (2) a second component composition comprising fibrinogen, fibrinogen-analog or fibrin monomer,
      wherein the fibrin-homolog is non-covalently bonded to the fibrinogen, fibrinogen-analog or fibrin monomer.

6. The fibrin-related mix polymer composition of claim 5, wherein the fibrin-homolog, fibrinogen, fibrinogen-analog or fibrin monomer are human proteins.

7. The fibrin-related mix polymer composition of claim 5, wherein the second component composition comprises fibrinogen or fibrinogen-analog.

8. The fibrin-related mix polymer composition of claim 7, wherein the second component composition is essentially free of fibrin monomer.

9. A fibrin sealant kit comprising:
   (1) a fibrin-homolog composition comprising a modified fibrin gamma-chain that differs from naturally occuing human fibrin gamma-chain by one or more mutations deletions or modifications in a C-terminal region following a coiled-coil forming region such that, when incorporated into fibrin-homolog, the homolog lacks the ability to substantially self-polymerize but has the ability to form non-covalent bonds with fibrinogen; and
   (2) a second component composition comprising fibrinogen, fibrinogen-analog or fibrin monomer,
      wherein the fibrin-homolog reacts with the fibrinogen, fibrinogen-analog or fibrin monomer to form a fibrin polymer.

10. The fibrin sealant kit of claim 9, wherein the fibrin-homolog, fibrinogen, fibrinogen-analog or fibrin monomer are human proteins.

11. The fibrin sealant kit of claim 9, wherein the second component composition comprises fibrinogen or fibrinogen-analog.

12. The fibrin sealant kit of claim 11, wherein the second component composition is essentially free of fibrin monomer.

13. A nucleotide sequence encoding a recombinant varian fibrin gamma-chain that differs from naturally occurring human fibrin gamma-chain by one or more mutations or deletions in a C-terminal region following a coiled-coil forming region such that, when incorporated into fibrin-homolog, the homolog lacks the ability to substantially self-polymerize but has the ability to form non-covalent bonds with fibrinogen.

14. An expression vector comprising the nucleotide sequence of claim 13, wherein said sequence is operably linked to a promoter which regulates the expression of said sequence.

15. The nucleotide sequence encoding a recombinant variant fibrin gamma-chain of claim 13, wherein the mutations or deletions occur in the sequence between about the position corresponding to the position of the first of the two conserved Cys residues found in the C-terminal portion of non-variant gamma-chains and the C-terminal.

16. The nucleotide sequence of claim 15, wherein the recombinant variant fibrin gamma-chain has a mutation or deletion of a Cys residue selected from the group consisting of Cys residues 352 and 365 of the human gamma-chain.

17. A cell comprising a nucleotide sequence encoding a recombinant variant fibrin gamma-chain that differs from naturally occurring human fibrin gamma-chain by one or more mutations or deletions in a C-terminal region following a coiled-coil forming region such that, when incorporated into fibrin-homolog, the homolog lacks the ability to substantially self-polymerize but has the ability to form non-covalent bonds with fibrinogen, wherein said sequence is operably linked to a promoter which regulates the expression of said sequence.

18. A method for producing a recombinant variant fibrin gamma-chain, which method comprises: growing the cell of claim 17 such that the variant gamma-chain is produced by said cell and recovering the variant gamma-chain.

19. A cell comprising:
   (i) an expression vector comprising a sequence encoding one of a fibrin alpha-chain or a fibrin alpha-chain with an N-terminal extension,
   (ii) an expression vector comprising a sequence encoding one of a fibrin beta-chain or a fibrin beta-chain with an N-terminal extension, and
   (iii) an expression vector comprising a sequence encoding a recombinant variant fibrin gamma-chain that differs from naturally occurring human fibrin gamma-chain by one or more mutations or deletions in a C-terminal region following a coiled-coil forming region such that, when incorporated into fibrin-homolog, the homolog lacks the ability to substantially self-polymerize but has the ability to form non-covalent bonds with fibrinogen, wherein each said coding sequence is operably linked to a promoter which regulates the expression of said sequence, and wherein the expression vectors of (i)–(iii) can be the same or different from each other.

20. The cell of claim 19, wherein the mutations or deletions in the recombinant variant fibrin gamma-chain occur in the sequence between about the position of the first of the two conserved Cys residues found in the C-terminal portion of the gamma-chain and the C-terminal.

21. The cell of claim 20, wherein the variant fibrin gamma-chain has a mutation or deletion of a Cys residue selected from the group consisting of Cys residues 352 and 365 of the human gamma-chain.

22. A method forming a fibrin polymer sealant, the method comprising a reacting a first fibrin-related protein that is incapable of self-polymerizing with a second fibrin-related protein that is incapable of self-polymerizing wherein said first fibrin-related protein is a fibrin homolog comprising a recombinant variant fibrin gamma-chain that differs from naturally occurring human fibrin gamma-chain by one or more mutations or deletions in a C-terminal region following a coiled-coil forming region such that, when incorporated into fibrin-homolog, the homolog lacks the ability to substantially self-polymerize but has the ability to form non-covalent bonds and thereby polymerize with fibrinogen.

23. The method for forming a fibrin polymer sealant of claim 22, wherein the mutations or deletions occur in the sequence between the position of the first of the two conserved Cys residues found in the C-terminal portion of fibrin gamma-chains and the C-terminal.

24. The method for forming a fibrin polymer sealant of claim 23, wherein the fibrin gamma-chain have a mutation, deletion or modification of a Cys residue selected from the group consisting of Cys residues 352 and 365 of the human fibrin gamma-chain.

25. The method for forming a fibrin polymer sealant of claim 22, wherein the second fibrin-related protein comprises at least one of fibrinogen or fibrinogen-analog.

26. The method for forming a fibrin polymer sealant of claim 25, wherein the second fibrin-related protein consists essentially of fibrinogen or fibrinogen-analog.

27. The method for forming a fibrin polymer sealant of claim 22 wherein, of the fibrin-related proteins, proteins that self-polymerize comprise no more than about 20% wt/wt.

28. The method for forming a fibrin polymer sealant of claim 22, wherein the first and second fibrin-related proteins are mixed in a ratio ranging from about 2:1 to about 1:2.

29. The method for forming a fibrin polymer sealant of claim 28, wherein the first and second fibrin-related proteins are mixed in a ratio ranging from about 1.5:1 to about 1:1.5.

* * * * *

SEQUENCE LISTING (1) GENERAL INFORMATION:

(iii) NUMBER OF SEQUENCES: 37

(2) INFORMATION FOR SEQ ID NO:1:

(i) SEQUENCE CHARACTERISTICS:
          (A) LENGTH: 97 base pairs
          (B) TYPE: nucleic acid
          (C) STRANDEDNESS: single
          (D) TOPOLOGY: linear (xi) SEQUENCE DESCRIPTION: SEQ ID NO:1:

CGTCGACTAG GAGCCAGCCC CACCCTTAGA AAAGATGTTT TCCATGAGGA TCGTCTGCCT      60

GGTCCTAAGT GTGGTGGGCA CAGCATGGAC TGGCCCA                              97

(2) INFORMATION FOR SEQ ID NO:2:

(i) SEQUENCE CHARACTERISTICS:
          (A) LENGTH: 105 base pairs
          (B) TYPE: nucleic acid
          (C) STRANDEDNESS: single
          (D) TOPOLOGY: linear (xi) SEQUENCE DESCRIPTION: SEQ ID NO:2:

CGCGTGGGCC AGTCCATGCT GTGCCCACCA CACTTAGGAC CAGGCAGACG ATCCTCATGG      60

AAAACATCTT TTCTAAGGGT GGGGCTGGCT CCTAGTCGAC GGTAC                     105

(2) INFORMATION FOR SEQ ID NO:3:

(i) SEQUENCE CHARACTERISTICS:
          (A) LENGTH: 136 base pairs
          (B) TYPE: nucleic acid
          (C) STRANDEDNESS: single
          (D) TOPOLOGY: linear (xi) SEQUENCE DESCRIPTION: SEQ ID NO:3:

CGTCGACATG AAAAGGATGG TTTCTTGGAG CTTCCACAAA CTTAAAACCA TGAAACATCT      60

ATTATTGCTA CTATTGTGTG TTTTTCTAGT TAAGTCCGGT CATCGACCCC TTGACAAGAA     120

GAGAGAAGAG GCTCCA                                                     136

(2) INFORMATION FOR SEQ ID NO:4:

(i) SEQUENCE CHARACTERISTICS:
          (A) LENGTH: 144 base pairs
          (B) TYPE: nucleic acid
          (C) STRANDEDNESS: single
          (D) TOPOLOGY: linear (xi) SEQUENCE DESCRIPTION: SEQ ID NO:4:

AGCTTGGAGC CTCTTCTCTC TTCTTGTCAA GGGGTCGATG ACCGGACTTA ACTAGAAAAA      60

CACACAATAG TAGCAATAAT AGATGTTTCA TGGTTTTAAG TTTGTGGAAG CTCCAAGAAA     120

CCATCCTTTT CATGTCGACG GTAC                                            144

(2) INFORMATION FOR SEQ ID NO:5:

(i) SEQUENCE CHARACTERISTICS:
          (A) LENGTH: 48 base pairs
          (B) TYPE: nucleic acid
          (C) STRANDEDNESS: single
          (D) TOPOLOGY: linear (xi) SEQUENCE DESCRIPTION: SEQ ID NO:5:

CTAGGGGGAG CCAAACAGGC TGGAGACGTT TAAGCGGCCG CAAGCTTG         48

(2) INFORMATION FOR SEQ ID NO:6:

(i) SEQUENCE CHARACTERISTICS:
        (A) LENGTH: 48 base pairs
        (B) TYPE: nucleic acid
        (C) STRANDEDNESS: single
        (D) TOPOLOGY: linear (xi) SEQUENCE DESCRIPTION: SEQ ID NO:6:

AATTCAAGCT TGCGGCCGCT TAAACGTCTC CAGCCTGTTT GGCTCCCC         48

(2) INFORMATION FOR SEQ ID NO:7:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (xi) SEQUENCE DESCRIPTION: SEQ ID NO:7:

CATGGCAGCT         10

(2) INFORMATION FOR SEQ ID NO:8:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (xi) SEQUENCE DESCRIPTION: SEQ ID NO:8:

GGGAAGCTTA CGCGTTGTGG AAAGACATCA ATCT         34

(2) INFORMATION FOR SEQ ID NO:9:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:9:

TAAGTGTTGC CTATCTCTAG A         21

(2) INFORMATION FOR SEQ ID NO:10:

(i) SEQUENCE CHARACTERISTICS:
        (A) LENGTH: 54 base pairs
        (B) TYPE: nucleic acid
        (C) STRANDEDNESS: single
        (D) TOPOLOGY: linear (xi) SEQUENCE DESCRIPTION: SEQ ID NO:10:

CGTCGACTAG GAGCCAGCCC CAGCCCCACC CTTAGAAAAG ATGTTTTCCA TGAG         54

(2) INFORMATION FOR SEQ ID NO:11:

(i) SEQUENCE CHARACTERISTICS:
        (A) LENGTH: 61 base pairs
        (B) TYPE: nucleic acid
        (C) STRANDEDNESS: single
        (D) TOPOLOGY: linear (xi) SEQUENCE DESCRIPTION: SEQ ID NO:11:

CAGACGATCC TCATGGAAAA CATCTTTTCT AAGGGTGGGG CTGGCTCCTA GTCGACGGTA          60

C          61

(2) INFORMATION FOR SEQ ID NO:12:

(i) SEQUENCE CHARACTERISTICS:
        (A) LENGTH: 49 base pairs
        (B) TYPE: nucleic acid
        (C) STRANDEDNESS: single
        (D) TOPOLOGY: linear (xi) SEQUENCE DESCRIPTION: SEQ ID NO:12:

GATCGTCTGC CTGGTCCTAA GTGTGGTGGG CACAGCATGG ACTGGCCCA          49

(2) INFORMATION FOR SEQ ID NO:13:

(i) SEQUENCE CHARACTERISTICS:
        (A) LENGTH: 44 base pairs
        (B) TYPE: nucleic acid
        (C) STRANDEDNESS: single
        (D) TOPOLOGY: linear (xi) SEQUENCE DESCRIPTION: SEQ ID NO:13:

CGCGTGGGCC AGTCCATGCT GTGCCCACCA CACTTAGGAC CAGG          44

(2) INFORMATION FOR SEQ ID NO:14:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (xi) SEQUENCE DESCRIPTION: SEQ ID NO:14:

TTTAAGCTTG AGGCCTGCCC CACCGC          26

(2) INFORMATION FOR SEQ ID NO:15:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:15:

GCAACATTTC CAAATCCCTG          20

(2) INFORMATION FOR SEQ ID NO:16:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (xi) SEQUENCE DESCRIPTION: SEQ ID NO:16:

CGTCGACATG AAAAGGATGG TTTCTTGGAG CTTCCACAAA CT          42

(2) INFORMATION FOR SEQ ID NO:17:

(i) SEQUENCE CHARACTERISTICS:
        (A) LENGTH: 55 base pairs
        (B) TYPE: nucleic acid
        (C) STRANDEDNESS: single
        (D) TOPOLOGY: linear (xi) SEQUENCE DESCRIPTION: SEQ ID NO:17:

ATGGTTTTAA GTTTGTGGAA GCTCCAAGAA ACCATCCTTT TCATGTCGAC GGTAC     55

(2) INFORMATION FOR SEQ ID NO:18:

(i) SEQUENCE CHARACTERISTICS:
        (A) LENGTH: 49 base pairs
        (B) TYPE: nucleic acid
        (C) STRANDEDNESS: single
        (D) TOPOLOGY: linear (xi) SEQUENCE DESCRIPTION: SEQ ID NO:18:

TAAAACCATG AAACATCTAT TATTGCTACT ATTGTGTGTT TTTCTAGTT     49

(2) INFORMATION FOR SEQ ID NO:19:

(i) SEQUENCE CHARACTERISTICS:
        (A) LENGTH: 49 base pairs
        (B) TYPE: nucleic acid
        (C) STRANDEDNESS: single
        (D) TOPOLOGY: linear (xi) SEQUENCE DESCRIPTION: SEQ ID NO:19:

ACCGGACTTA ACTAGAAAAA CACACAATAG TAGCAATAAT AGATGTTTC     49

(2) INFORMATION FOR SEQ ID NO:20:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (xi) SEQUENCE DESCRIPTION: SEQ ID NO:20:

AAGTCCGGTC ATCGACCCCT TGACAAGAAG AGAGAAGAGG CTCCA     45

(2) INFORMATION FOR SEQ ID NO:21:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (xi) SEQUENCE DESCRIPTION: SEQ ID NO:21:

AGCTTGGAGC CTCTTCTCTC TTCTTGTCAA GGGGTCGATG     40

(2) INFORMATION FOR SEQ ID NO:22:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (xi) SEQUENCE DESCRIPTION: SEQ ID NO:22:

CACTCCCATA ATGGCATGC     19

(2) INFORMATION FOR SEQ ID NO:23:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (xi) SEQUENCE DESCRIPTION: SEQ ID NO:23:

CACGAATTCC CTAGGTGGTG TTGCTGTCC                                    29

(2) INFORMATION FOR SEQ ID NO:24:

(i) SEQUENCE CHARACTERISTICS:
        (A) LENGTH: 48 base pairs
        (B) TYPE: nucleic acid
        (C) STRANDEDNESS: single
        (D) TOPOLOGY: linear (xi) SEQUENCE DESCRIPTION: SEQ ID NO:24:

CTAGGGGGAG CCAAACAGGC TGGAGACGTT TAAGCGGCCG CAAGCTTG              48

(2) INFORMATION FOR SEQ ID NO:25:

(i) SEQUENCE CHARACTERISTICS:
        (A) LENGTH: 48 base pairs
        (B) TYPE: nucleic acid
        (C) STRANDEDNESS: single
        (D) TOPOLOGY: linear (xi) SEQUENCE DESCRIPTION: SEQ ID NO:25:

AATTCAAGCT TGCGGCCGCT TAAACGTCTC CAGCCTGTTT GGCTCCCC              48

(2) INFORMATION FOR SEQ ID NO:26:

(i) SEQUENCE CHARACTERISTICS:
        (A) LENGTH: 1438 base pairs
        (B) TYPE: nucleic acid
        (C) STRANDEDNESS: double
        (D) TOPOLOGY: linear (ix) FEATURE:
        (A) NAME/KEY: Coding Sequence
        (B) LOCATION: 3...1364
        (D) OTHER INFORMATION:

(xi) SEQUENCE DESCRIPTION: SEQ ID NO:26:

```
GG TAC CGG GCC CCC CCT CGA GGT CGA CCG CGG CCC CCC GGG CAC TCA            47
   Tyr Arg Ala Pro Pro Arg Gly Arg Pro Arg Pro Pro Gly His Ser
    1               5                  10                  15

GAC ATC ATG AGT TGG TCC TTG CAC CCC CGG AAT TTA ATT CTC TAC TTC           95
Asp Ile Met Ser Trp Ser Leu His Pro Arg Asn Leu Ile Leu Tyr Phe
                 20                  25                  30

TAT GCT CTT TTA TTT CTC TCT TCA ACA TGT GTA GCA TAT GTT GCT ACC          143
Tyr Ala Leu Leu Phe Leu Ser Ser Thr Cys Val Ala Tyr Val Ala Thr
             35                  40                  45

AGA GAC AAC TGC TGC ATC TTA GAT GAA AGA TTC GGT AGT TAT TGT CCA          191
Arg Asp Asn Cys Cys Ile Leu Asp Glu Arg Phe Gly Ser Tyr Cys Pro
         50                  55                  60

ACT ACC TGT GGC ATT GCA GAT TTC CTG TCT ACT TAT CAA ACC AAA GTA          239
Thr Thr Cys Gly Ile Ala Asp Phe Leu Ser Thr Tyr Gln Thr Lys Val
     65                  70                  75

GAC AAG GAT CTA CAG TCT TTG GAA GAC ATC TTA CAT CAA GTT GAA AAC          287
Asp Lys Asp Leu Gln Ser Leu Glu Asp Ile Leu His Gln Val Glu Asn
 80                  85                  90                  95

AAA ACA TCA GAA GTC AAA CAG CTG ATA AAA GCA ATC CAA CTC ACT TAT          335
Lys Thr Ser Glu Val Lys Gln Leu Ile Lys Ala Ile Gln Leu Thr Tyr
                100                 105                 110

AAT CCT GAT GAA TCA TCA AAA CCA GAT ATG ATA GAC GCT GCT ACT TTG          383
Asn Pro Asp Glu Ser Ser Lys Pro Asp Met Ile Asp Ala Ala Thr Leu
            115                 120                 125

AAG TCC AGG ATA ATG TTA GAA GAA ATT ATG AAA TAT GAA GCA TCG ATT          431
```

-continued

```
                Lys Ser Arg Ile Met Leu Glu Glu Ile Met Lys Tyr Glu Ala Ser Ile
                            130                 135                 140

TTA ACA CAT GAC TCA AGT ATT CGG TAT TTG CAG GAA ATA TAT AAT TCA              479
Leu Thr His Asp Ser Ser Ile Arg Tyr Leu Gln Glu Ile Tyr Asn Ser
145                 150                 155

AAT AAT CAA AAG ATT GTT AAC CTG AAA GAG AAG GTA GCC CAG CTT GAA              527
Asn Asn Gln Lys Ile Val Asn Leu Lys Glu Lys Val Ala Gln Leu Glu
160                 165                 170                 175

GCA CAG TGC CAG GAA CCT TGC AAA GAC ACG GTG CAA ATC CAT GAT ATC              575
Ala Gln Cys Gln Glu Pro Cys Lys Asp Thr Val Gln Ile His Asp Ile
                180                 185                 190

ACT GGG AAA GAT TGT CAA GAC ATT GCC AAT AAG GGA GCT AAA CAG AGC              623
Thr Gly Lys Asp Cys Gln Asp Ile Ala Asn Lys Gly Ala Lys Gln Ser
            195                 200                 205

GGG CTT TAC TTT ATT AAA CCT CTG AAA GCT AAC CAG CAA TTC TTA GTC              671
Gly Leu Tyr Phe Ile Lys Pro Leu Lys Ala Asn Gln Gln Phe Leu Val
            210                 215                 220

TAC TGT GAA ATC GAT GGG TCT GGA AAT GGA TGG ACT GTG TTT CAG AAG              719
Tyr Cys Glu Ile Asp Gly Ser Gly Asn Gly Trp Thr Val Phe Gln Lys
225                 230                 235

AGA CTT GAT GGC AGT GTA GAT TTC AAG AAA AAC TGG ATT CAA TAT AAA              767
Arg Leu Asp Gly Ser Val Asp Phe Lys Lys Asn Trp Ile Gln Tyr Lys
240                 245                 250                 255

GAA GGA TTT GGA CAT CTG TCT CCT ACT GGC ACA ACA GAA TTT TGG CTG              815
Glu Gly Phe Gly His Leu Ser Pro Thr Gly Thr Thr Glu Phe Trp Leu
                260                 265                 270

GGA AAT GAG AAG ATT CAT TTG ATA AGC ACA CAG TCT GCC ATC CCA TAT              863
Gly Asn Glu Lys Ile His Leu Ile Ser Thr Gln Ser Ala Ile Pro Tyr
            275                 280                 285

GCA TTA AGA GTG GAA CTG GAA GAC TGG AAT GGC AGA ACC AGG ACT GCA              911
Ala Leu Arg Val Glu Leu Glu Asp Trp Asn Gly Arg Thr Arg Thr Ala
            290                 295                 300

GAC TAT GCC ATG TTC AAG GTG GGA CCT GAA GCT GAC AAG TAC CGC CTA              959
Asp Tyr Ala Met Phe Lys Val Gly Pro Glu Ala Asp Lys Tyr Arg Leu
305                 310                 315

ACA TAT GCC TAC TTC GCT GGT GGG GAT GCT GGA GAT GCC TTT GAT GGC             1007
Thr Tyr Ala Tyr Phe Ala Gly Gly Asp Ala Gly Asp Ala Phe Asp Gly
320                 325                 330                 335

TTT GAT TTT GGC GAT GAT CCT AGT GAC AAG TTT TTC ACA TCC CAT AAT             1055
Phe Asp Phe Gly Asp Asp Pro Ser Asp Lys Phe Phe Thr Ser His Asn
                340                 345                 350

GGC ATG CAG TTC AGT ACC TGG GAC AAT GAC AAT GAT AAG TTT GAA GGC             1103
Gly Met Gln Phe Ser Thr Trp Asp Asn Asp Asn Asp Lys Phe Glu Gly
            355                 360                 365

AAC GCT GCT GAA CAG GAT GGA TCT GGT TGG TGG ATG AAC AAG GCT CAC             1151
Asn Ala Ala Glu Gln Asp Gly Ser Gly Trp Trp Met Asn Lys Ala His
            370                 375                 380

GCT GGC CAT CTC AAT GGA GTT TAT TAC CAA GGT GGC ACT TAC TCA AAA             1199
Ala Gly His Leu Asn Gly Val Tyr Tyr Gln Gly Gly Thr Tyr Ser Lys
385                 390                 395

GCA TCT ACT CCT AAT GGT TAT GAT AAT GGC ATT ATT TGG GCC ACT TGG             1247
Ala Ser Thr Pro Asn Gly Tyr Asp Asn Gly Ile Ile Trp Ala Thr Trp
400                 405                 410                 415

AAA ACC CGG TGG TAT TCC ATG AAG AAA ACC ACT ATG AAG ATA ATC CCA             1295
Lys Thr Arg Trp Tyr Ser Met Lys Lys Thr Thr Met Lys Ile Ile Pro
                420                 425                 430

TTC AAC AGA CTC ACA ATT GGA GAA GGA CAG CAA CAC CAC CTG GGG GGA             1343
Phe Asn Arg Leu Thr Ile Gly Glu Gly Gln Gln His His Leu Gly Gly
            435                 440                 445
```

```
GCC AAA CAG GCT GGA GAC GTT TAAAAGACCG TTTCAAAAGA GATTTACTTT TTTA        1398
Ala Lys Gln Ala Gly Asp Val
            450

AAGGACTTTA TCTGAACAGA GAGATATAAT GGGCGGCCGC                              1438
```

(2) INFORMATION FOR SEQ ID NO:27:

(i) SEQUENCE CHARACTERISTICS:
        (A) LENGTH: 454 amino acids
        (B) TYPE: amino acid
        (C) STRANDEDNESS: single
        (D) TOPOLOGY: linear (ii) MOLECULE TYPE: protein (v) FRAGMENT TYPE: internal (xi) SEQUENCE DESCRIPTION: SEQ ID NO:27:

```
Tyr Arg Ala Pro Pro Arg Gly Arg Pro Arg Pro Gly His Ser Asp
 1               5                  10                  15

Ile Met Ser Trp Ser Leu His Pro Arg Asn Leu Ile Leu Tyr Phe Tyr
            20                  25                  30

Ala Leu Leu Phe Leu Ser Ser Thr Cys Val Ala Tyr Val Ala Thr Arg
            35                  40                  45

Asp Asn Cys Cys Ile Leu Asp Glu Arg Phe Gly Ser Tyr Cys Pro Thr
 50                      55                  60

Thr Cys Gly Ile Ala Asp Phe Leu Ser Thr Tyr Gln Thr Lys Val Asp
 65                  70                  75                  80

Lys Asp Leu Gln Ser Leu Glu Asp Ile Leu His Gln Val Glu Asn Lys
                85                  90                  95

Thr Ser Glu Val Lys Gln Leu Ile Lys Ala Ile Gln Leu Thr Tyr Asn
                100                 105                 110

Pro Asp Glu Ser Ser Lys Pro Asp Met Ile Asp Ala Ala Thr Leu Lys
                115                 120                 125

Ser Arg Ile Met Leu Glu Glu Ile Met Lys Tyr Glu Ala Ser Ile Leu
            130                 135                 140

Thr His Asp Ser Ser Ile Arg Tyr Leu Gln Glu Ile Tyr Asn Ser Asn
145                 150                 155                 160

Asn Gln Lys Ile Val Asn Leu Lys Glu Lys Val Ala Gln Leu Glu Ala
                165                 170                 175

Gln Cys Gln Glu Pro Cys Lys Asp Thr Val Gln Ile His Asp Ile Thr
            180                 185                 190

Gly Lys Asp Cys Gln Asp Ile Ala Asn Lys Gly Ala Lys Gln Ser Gly
            195                 200                 205

Leu Tyr Phe Ile Lys Pro Leu Lys Ala Asn Gln Gln Phe Leu Val Tyr
    210                 215                 220

Cys Glu Ile Asp Gly Ser Gly Asn Gly Trp Thr Val Phe Gln Lys Arg
225                 230                 235                 240

Leu Asp Gly Ser Val Asp Phe Lys Lys Asn Trp Ile Gln Tyr Lys Glu
                245                 250                 255

Gly Phe Gly His Leu Ser Pro Thr Gly Thr Thr Glu Phe Trp Leu Gly
            260                 265                 270

Asn Glu Lys Ile His Leu Ile Ser Thr Gln Ser Ala Ile Pro Tyr Ala
        275                 280                 285

Leu Arg Val Glu Leu Glu Asp Trp Asn Gly Arg Thr Arg Thr Ala Asp
    290                 295                 300

Tyr Ala Met Phe Lys Val Gly Pro Glu Ala Asp Lys Tyr Arg Leu Thr
```

-continued

```
                305                 310                 315                 320

Tyr Ala Tyr Phe Ala Gly Gly Asp Ala Gly Asp Ala Phe Asp Gly Phe
                    325                 330                 335

Asp Phe Gly Asp Asp Pro Ser Asp Lys Phe Phe Thr Ser His Asn Gly
                340                 345                 350

Met Gln Phe Ser Thr Trp Asp Asn Asp Asn Asp Lys Phe Glu Gly Asn
                355                 360                 365

Ala Ala Glu Gln Asp Gly Ser Gly Trp Trp Met Asn Lys Ala His Ala
            370                 375                 380

Gly His Leu Asn Gly Val Tyr Tyr Gln Gly Gly Thr Tyr Ser Lys Ala
385                 390                 395                 400

Ser Thr Pro Asn Gly Tyr Asp Asn Gly Ile Ile Trp Ala Thr Trp Lys
                    405                 410                 415

Thr Arg Trp Tyr Ser Met Lys Lys Thr Thr Met Lys Ile Ile Pro Phe
                420                 425                 430

Asn Arg Leu Thr Ile Gly Glu Gly Gln Gln His His Leu Gly Gly Ala
                435                 440                 445

Lys Gln Ala Gly Asp Val
            450
```

(2) INFORMATION FOR SEQ ID NO:28:

(i) SEQUENCE CHARACTERISTICS:
        (A) LENGTH: 454 amino acids
        (B) TYPE: amino acid
        (C) STRANDEDNESS: single
        (D) TOPOLOGY: linear (xi) SEQUENCE DESCRIPTION: SEQ ID NO:28:

```
Tyr Arg Ala Pro Pro Arg Gly Arg Pro Arg Pro Pro Gly His Ser Asp
1               5                   10                  15

Ile Met Ser Trp Ser Leu His Pro Arg Asn Leu Ile Leu Tyr Phe Tyr
                20                  25                  30

Ala Leu Leu Phe Leu Ser Ser Thr Cys Val Ala Tyr Val Ala Thr Arg
                35                  40                  45

Asp Asn Cys Cys Ile Leu Asp Glu Arg Phe Gly Ser Tyr Cys Pro Thr
            50                  55                  60

Thr Cys Gly Ile Ala Asp Phe Leu Ser Thr Tyr Gln Thr Lys Val Asp
65                  70                  75                  80

Lys Asp Leu Gln Ser Leu Glu Asp Ile Leu His Gln Val Glu Asn Lys
                85                  90                  95

Thr Ser Glu Val Lys Gln Leu Ile Lys Ala Ile Gln Leu Thr Tyr Asn
                100                 105                 110

Pro Asp Glu Ser Ser Lys Pro Asp Met Ile Asp Ala Ala Thr Leu Lys
            115                 120                 125

Ser Arg Ile Met Leu Glu Glu Ile Met Lys Tyr Glu Ala Ser Ile Leu
130                 135                 140

Thr His Asp Ser Ser Ile Arg Tyr Leu Gln Glu Ile Tyr Asn Ser Asn
145                 150                 155                 160

Asn Gln Lys Ile Val Asn Leu Lys Glu Lys Val Ala Gln Leu Glu Ala
                165                 170                 175

Gln Cys Gln Glu Pro Cys Lys Asp Thr Val Gln Ile His Asp Ile Thr
            180                 185                 190

Gly Lys Asp Cys Gln Asp Ile Ala Asn Lys Gly Ala Lys Gln Ser Gly
                195                 200                 205
```

```
Leu Tyr Phe Ile Lys Pro Leu Lys Ala Asn Gln Gln Phe Leu Val Tyr
    210                 215                 220

Cys Glu Ile Asp Gly Ser Gly Asn Gly Trp Thr Val Phe Gln Lys Arg
225                 230                 235                 240

Leu Asp Gly Ser Val Asp Phe Lys Lys Asn Trp Ile Gln Tyr Lys Glu
                245                 250                 255

Gly Phe Gly His Leu Ser Pro Thr Gly Thr Thr Glu Phe Trp Leu Gly
                260                 265                 270

Asn Glu Lys Ile His Leu Ile Ser Thr Gln Ser Ala Ile Pro Tyr Ala
    275                 280                 285

Leu Arg Val Glu Leu Glu Asp Trp Asn Gly Arg Thr Arg Thr Ala Asp
    290                 295                 300

Tyr Ala Met Phe Lys Val Gly Pro Glu Ala Asp Lys Tyr Arg Leu Thr
305                 310                 315                 320

Tyr Ala Tyr Phe Ala Gly Gly Asp Ala Gly Asp Ala Phe Asp Gly Phe
                325                 330                 335

Asp Phe Gly Asp Asp Pro Ser Asp Lys Phe Phe Thr Ser His Asn Gly
                340                 345                 350

Met Gln Phe Ser Thr Trp Asp Asn Asp Asn Asp Lys Phe Glu Gly Asn
    355                 360                 365

Ala Ala Glu Gln Asp Gly Ser Gly Trp Trp Met Asn Lys Ala His Ala
    370                 375                 380

Gly His Leu Asn Gly Val Tyr Tyr Gln Gly Gly Thr Tyr Ser Lys Ala
385                 390                 395                 400

Ser Thr Pro Asn Gly Tyr Asp Asn Gly Ile Ile Trp Ala Thr Trp Lys
                405                 410                 415

Thr Arg Trp Tyr Ser Met Lys Lys Thr Thr Met Lys Ile Ile Pro Phe
                420                 425                 430

Asn Arg Leu Thr Ile Gly Glu Gly Gln Gln His His Leu Gly Gly Ala
    435                 440                 445

Lys Gln Ala Gly Asp Val
    450

(2) INFORMATION FOR SEQ ID NO:29:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (xi) SEQUENCE DESCRIPTION: SEQ ID NO:29:

CATGGCAGCT                                                              10

(2) INFORMATION FOR SEQ ID NO:30:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (xi) SEQUENCE DESCRIPTION: SEQ ID NO:30:

TTTGAAGGCA ACGCTGCTGA ACAGGA                                            26

(2) INFORMATION FOR SEQ ID NO:31:

(i) SEQUENCE CHARACTERISTICS:
        (A) LENGTH: 28 base pairs
```

(B) TYPE: nucleic acid
        (C) STRANDEDNESS: single
        (D) TOPOLOGY: linear (xi) SEQUENCE DESCRIPTION: SEQ ID NO:31:

ACAAGGCTCA CGCTGGCCAT CTCAATGG                                         28

(2) INFORMATION FOR SEQ ID NO:32:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:32:

GATCCATCCT GTTCAGCAGC                                                  20

(2) INFORMATION FOR SEQ ID NO:33:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:33:

GGTTGGTGGA TGAACAAGGC                                                  20

(2) INFORMATION FOR SEQ ID NO:34:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (xi) SEQUENCE DESCRIPTION: SEQ ID NO:34:

CTAGCGCCGG GGTT                                                        14

(2) INFORMATION FOR SEQ ID NO:35:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (xi) SEQUENCE DESCRIPTION: SEQ ID NO:35:

GCGGCCCCAA                                                             10

(2) INFORMATION FOR SEQ ID NO:36:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:36:

AATTTCGTTA ACAAGCGCGG CCCACGCGTT GTGGAA                                36

(2) INFORMATION FOR SEQ ID NO:37:

(i) SEQUENCE CHARACTERISTICS:
        (A) LENGTH: 8 amino acids
        (B) TYPE: amino acid -continued

```
        (C) STRANDEDNESS: single
        (D) TOPOLOGY: linear (xi) SEQUENCE DESCRIPTION: SEQ ID NO:37:

Lys Arg Gly Pro Arg Val Val Glu
1               5
```